(12) United States Patent
Wei et al.

(10) Patent No.: US 6,987,014 B2
(45) Date of Patent: Jan. 17, 2006

(54) ISOLATED NUCLEIC ACID MOLECULES ENCODING HUMAN DRUG METABOLIZING PROTEINS

(75) Inventors: Ming-Hui Wei, Germantown, MD (US); Jane Ye, Boyds, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 997 days.

(21) Appl. No.: 09/784,340

(22) Filed: Feb. 16, 2001

(65) Prior Publication Data

US 2005/0208484 A1    Sep. 22, 2005

Related U.S. Application Data

(60) Provisional application No. 60/228,893, filed on Aug. 30, 2000.

(51) Int. Cl.
*C12N 9/10*     (2006.01)
*C12N 15/00*    (2006.01)
*C12N 1/20*     (2006.01)
*C12N 5/00*     (2006.01)
*C12Q 1/48*     (2006.01)

(52) U.S. Cl. ............ 435/193; 435/252.3; 435/320.1; 435/325; 435/69.1; 435/6; 435/15; 536/23.2; 530/350; 436/94

(58) Field of Classification Search ............ 435/193, 435/252.3, 325, 320.1, 6, 69.1, 15; 536/23.2; 436/94; 530/350
See application file for complete search history.

(56) References Cited

U.S. PATENT DOCUMENTS

2004/0029125 A1 * 2/2004 Policky et al. ............ 435/6
2004/0029221 A1 * 2/2004 Baker et al. ............ 435/69.1

FOREIGN PATENT DOCUMENTS

WO    WO 01/79468 A2 * 10/2001

OTHER PUBLICATIONS

Mackenzie, P. I. J. Biol.Chem. 261:6119-6125, 1986 (TrEMBL accesion No. A42233, 1992).*
Jin, C. J. et al. Biochem. Biophys. Res. Commun. 194:496-503, 1993 (TrEMBL accesion No. O75614, 1998).*
Sambrook and Russell, Molecular Cloning, Third Edition, CSHL Press, 2001.*
U.S. Appl. No. 60/197,590, Policky et al., filed Apr. 2000.*

* cited by examiner

*Primary Examiner*—Rebecca E. Prouty
*Assistant Examiner*—Delia M. Ramirez
(74) *Attorney, Agent, or Firm*—Celera Genomics; Lin Sun-Hoffman

(57) ABSTRACT

The present invention provides amino acid sequences of peptides that are encoded by genes within the human genome, the drug-metabolizing enzyme peptides of the present invention. The present invention specifically provides isolated peptide and nucleic acid molecules, methods of identifying orthologs and paralogs of the drug-metabolizing enzyme peptides, and methods of identifying modulators of the drug-metabolizing enzyme peptides.

12 Claims, 18 Drawing Sheets

```
   1 CAACCATTGC AGATCAGTGT GTGAGGGAAC TGCCATCATG AGGTCTGACA
  51 AGTCAGCTTT GGTATTTCTG CTCCTGCAGC TCTTCTGTGT TGGCTGTGGA
 101 TTCTGTGGGA AAGTCCTGGT GTGGCCCTGT GACATGAGCC ATTGGCTTAA
 151 TGTCAAGGTC ATTCTAGAAG AGCTCATAGT GAGAGGCCAT GAGGTAACAG
 201 TATTGACTCA CTCAAAGCCT TCGTTAATTG ACTACAGGAA GCCTTCTGCA
 251 TTGAAATTTG AGGTGGTCCA TATGCCACAG GACAGAACAG AAGAAAATGA
 301 AATATTTGTT GACCTAGCTC TGAATGTCTT GCCAGGCTTA TCAACCTGGC
 351 AATCAGTTAT AAAATTAAAT GATTTTTTTG TTGAAATAAG AGGAACTTTA
 401 AAAATGATGT GTGAGAGCTT TATCTACAAT CAGACGCTTA TGAAGAAGCT
 451 ACAGGAAACC AACTACGATG TAATGCTTAT AGACCCTGTG ATTCCCTGTG
 501 GAGACCTGAT GGCTGAGTTG CTTGCAGTCC CTTTTGTGCT CACACTTAGA
 551 ATTTCTGTAG GAGGCAATAT GGAGCGAAGC TGTGGGAAAC TTCCAGCTCC
 601 ACTTTCCTAT GTACCTGTGC CTATGACAGG ACTAACAGAC AGAATGACCT
 651 TTCTGGAAAG AGTAAAAAAT TCAATGCTTT CAGTTTTGTT CCACTTCTGG
 701 ATTCAGGATT ACGACTATCA TTTTTGGGAA GAGTTTTATA GTAAGGCATT
 751 AGGAAGGCCC ACTACATTAT GTGAGACTGT GGGAAAAGCT GAGATATGGC
 801 TAATACGAAC ATATTGGGAT TTTGAATTTC CTCAACCATA CCAACCTAAC
 851 TTTGAGTTTG TTGGAGGATT GCACTGTAAA CCTGCCAAAG CTTTGCCTAA
 901 GGAAATGGAA AATTTTGTCC AGAGTTCAGG GGAAGATGGT ATTGTGGTGT
 951 TTTCTCTGGG GTCACTGTTT CAAAATGTTA CAGAAGAAAA GGCTAATATC
1001 ATTGCTTCAG CCCTTGCCCA GATCCCACAG AAGGTGTTAT GGAGGTACAA
1051 AGGAAAAAAA CCATCCACAT TAGGAGCCAA TACTCGGCTG TATGATTGGA
1101 TACCCCAGAA TGATCTTCTT GGTCATCCCA AAACCAAAGC TTTTATCACT
1151 CATGGTGGAA TGAATGGGAT CTATGAAGCT ATTTACCATG GGGTCCCTAT
1201 GGTGGGAGTT CCCATATTTG GTGATCAGCT TGATAACATA GCTCACATGA
1251 AGGCCAAAGG AGCAGCTGTA GAAATAAACT TCAAAACTAT GACAAGCGAA
1301 GATTTACTGA GGGCTTTGAG AACAGTCATT ACCGATTCCT CTTATAAAGA
1351 GAATGCTATG AGATTATCAA GAATTCACCA TGATCAACCT GTAAAGCCCC
1401 TAGATCGAGC AGTCTTCTGG ATCGAGTTTG TCATGCGCCA CAAAGGAGCC
1451 AAGCACCTGC GATCAGCTGC CCATGACCTC ACCTGGTTCC AGCACTACTC
1501 TATAGATGTG ATTGGGTTCC TGCTGACCTG TGTGGCAACT GCTATATTCT
1551 TGTTCACAAA ATGTTTTTTA TTTTCCTGTC AAAAATTTAA TAAAACTAGA
1601 AAGATAGAAA AGAGGGAATA GATCTTTCCA AATTCAAGAA AGACCTGATG
1651 GGGTAATCCT GTTAATTCCA GCCACATAGA ATTTGGTGAA AACCTTGCTA
1701 TTTTCATATT ATCTATTCTG TTATTTTATC TTAGCTATAT AGCCTAGAAT
1751 TCCATGATCA TGAGGTTGTG AGTATATCTC ATTCTTTCGT TGCATTTTCC
1801 TAGGTGTGCT TACTCTCTTC TCTCACTTTG TGACACAAGG ACATGAATAC
1851 ATCTAAATTT TCCTATTTCT GATATCACTG TTTCCATGAC GTCATTACTT
1901 CTCTAACCTT AAGTGATAGG GTGACCTGCA ATATGCTGAT TCCTGGTGTT
1951 TGCACAAACA CATGGATGTA AAGAAGTAAA AAATGTAAAA TTCACAAAAT
2001 TCAGTAAACC ACACAAATCA ATGAAGCATT CTATGACATT AGCTTGTTAT
2051 GAGTAACATA ATGATTTTTC TTTTTCAATT TAAATAAGCC CTTCTACATA
2101 CCCAGCATTA CTGATCTCAG ACAATGAATT GCTAAAAATG ACGATAGGGC
2151 ATTACACTCA GAATAGTTTG CTATATTTCC ACATACCTCA TCTAGATGTC
2201 ATAGCCTACA TTTCTGCCAT CACTTAACTG ACATTTTTTG TGTGTTCTTG
2251 ATGATAAATA GACAGTTCTT ATTATTGTCC TCAAATAATA AAAGAAACTG
2301 AAATTTTCTT ACATAGAGAA AATGTCCATA AGATATTCAA GTTAAACAGA
2351 TTATTTTGAG ATAAGTAACC ATTAGAAATA TGTGATTGTA ATTTCTGATT
2401 TTATAAAATT TTAATTGATA GTACACTTGA TTTAAATGTC TATTCTTTAA
2451 AATGATGAAT ACTCATAATT CTTATCTCTA TAATCAAAAG TATAATTTAC
2501 TGTAGAAAAA TAAAGAGATG CTTGTTCTGA AAGTAAAAAA AAAAAAAAAA
2551 AAAACACTGT CATGCCGTTA CGTAGCGTAT CGTTGACAGC CCACTGTCAT
2601 GCCGTTACGT AGCATATCGT TGACAGCGAC ACTGTCATGC CGTTACGTAG
2651 CGTATCGTTG ACAGCACTGT CATGCGTTAC GAGCGTATCG TTGACAGCAC
2701 TGTCATGCCG TTACGTAGCG TATCGTTGAC AGCAAAACAC TGTCAGCCGT
2751 TACGTAGCG  (SEQ ID NO:1)
```

FIGURE 1A

FEATURES:
5'UTR:         1-37
Start Codon:   38
Stop Codon:    1619
3'UTR:         1622

Homologous proteins:
Top 10 BLAST Hits

```
                                                                         Score    E
CRA|147000022596013 /altid=gi|10438148 /def=dbj|BAB15179.1| (AK...        931    0.0
CRA|1000682322899  /altid=gi|5802604  /def=gb|AAD51732.1| (AF1752...      795    0.0
CRA|335001098690982 /altid=gi|11436851 /def=ref|XP_003547.1| UD...        679    0.0
CRA|18000005226060 /altid=gi|5803213  /def=ref|NP_006789.1| UDP ...       677    0.0
CRA|18000005155438 /altid=gi|4507821  /def=ref|NP_001068.1| UDP ...       676    0.0
CRA|18000005147363 /altid=gi|6175083  /def=sp|P06133|UDB4_HUMAN ...       675    0.0
CRA|18000004953169 /altid=gi|484383   /def=pir||JN0619 glucuronos...      674    0.0
CRA|18000005148770 /altid=gi|3153832  /def=gb|AAC95002.1| (AF064...       674    0.0
CRA|18000004903910 /altid=gi|4507819  /def=ref|NP_001067.1| UDP ...       669    0.0
CRA|18000005164461 /altid=gi|3426332  /def=gb|AAC32272.1| (AF081...       668    0.0
CRA|1000682327923  /altid=gi|5881246  /def=gb|AAD55093.1|AF180322...      668    0.0
CRA|18000005219476 /altid=gi|8134780  /def=sp|Q9XT55|UDBJ_MACFA ...       667    0.0
```

BLAST dbEST hits:
```
gi|10971169 /dataset=dbest /taxon=96...                                   383   .e-103
gi|11068678 /dataset=dbest /taxon=96...                                   234    6e-59
gi|679005   /dataset=dbest /taxon=9606 /...                               212    2e-52
gi|3173232  /dataset=dbest /taxon=9606 ...                                212    2e-52
gi|3134358  /dataset=dbest /taxon=9606 ...                                212    2e-52
gi|10298020 /dataset=dbest /taxon=96...                                   200    8e-49
gi|11974507 /dataset=dbest /taxon=96...                                   196    1e-47
gi|11973717 /dataset=dbest /taxon=96...                                   172    2e-40
gi|12673874 /dataset=dbest /taxon=96...                                   137    1e-29
gi|10887798 /dataset=dbest /taxon=96...                                   125    4e-26
```

EXPRESSION INFORMATION FOR MODULATORY USE:
library source:
Expression information from BLAST dbEST hits:
gi|10971169 Kidney-hypernephroma
gi|11068678 HepG2 cell line
gi|679005   Liver
gi|3173232  Kidney
gi|3134358  Kidney
gi|10298020 Hepatocellular carcinoma
gi|11974507 Normal pigmental retinal epithelium
gi|11973717 Normal pigmental retinal epithelium
gi|12673874 Kidney hypernephroma
gi|10887798 Kidney Expression information from PCR-based tissue screening panels:
Human fetal liver

FIGURE 1B

```
  1 MRSDKSALVF LLLQLFCVGC GFCGKVLVWP CDMSHWLNVK VILEELIVRG
 51 HEVTVLTHSK PSLIDYRKPS ALKFEVVHMP QDRTEENEIF VDLALNVLPG
101 LSTWQSVIKL NDFFVEIRGT LKMMCESFIY NQTLMKKLQE TNYDVMLIDP
151 VIPCGDLMAE LLAVPFVLTL RISVGGNMER SCGKLPAPLS YVPVPMTGLT
201 DRMTFLERVK NSMLSVLFHF WIQDYDYHFW EEFYSKALGR PTTLCETVGK
251 AEIWLIRTYW DFEFPQPYQP NFEFVGGLHC KPAKALPKEM ENFVQSSGED
301 GIVVFSLGSL FQNVTEEKAN IIASALAQIP QKVLWRYKGK KPSTLGANTR
351 LYDWIPQNDL LGHPKTKAFI THGGMNGIYE AIYHGVPMVG VPIFGDQLDN
401 IAHMKAKGAA VEINFKTMTS EDLLRALRTV ITDSSYKENA MRLSRIHHDQ
451 PVKPLDRAVF WIEFVMRHKG AKHLRSAAHD LTWFQHYSID VIGFLLTCVA
501 TAIFLFTKCF LFSCQKFNKT RKIEKRE   (SEQ ID NO:2)
```

FEATURES:
Functional domains and key regions:
[1] PDOC00001 PS00001 ASN_GLYCOSYLATION
N-glycosylation site Number of matches: 3
    1    131-134 NQTL
    2    313-316 NVTE
    3    518-521 NKTR

[2] PDOC00004 PS00004 CAMP_PHOSPHO_SITE
cAMP- and cGMP-dependent protein kinase phosphorylation site Number of matches: 2
    1    67-70 RKPS
    2    340-343 KKPS

[3] PDOC00005 PS00005 PKC_PHOSPHO_SITE
Protein kinase C phosphorylation site

Number of matches: 6
    1    3-5 SDK
    2    120-122 TLK
    3    169-171 TLR
    4    200-202 TDR
    5    435-437 SYK
    6    520-522 TRK

[4] PDOC00006 PS00006 CK2_PHOSPHO_SITE
Casein kinase II phosphorylation site

Number of matches: 9
    1    62-65 SLID
    2    141-144 TNYD
    3    204-207 TFLE
    4    243-246 TLCE
    5    258-261 TYWD
    6    296-299 SSGE
    7    297-300 SGED
    8    419-422 TSED
    9    435-438 SYKE

[5] PDOC00007 PS00007 TYR_PHOSPHO_SITE
Tyrosine kinase phosphorylation site

FIGURE 2A

```
Number of matches: 2
      1     122-130   KMMCESFIY
      2     136-143   KKLQETNY

[6] PDOC00008 PS00008 MYRISTYL
N-myristoylation site

Number of matches: 4
      1      19-24    GCGFCG
      2     276-281   GGLHCK
      3     373-378   GGMNGI
      4     377-382   GIYEAI

[7] PDOC00009 PS00009 AMIDATION
Amidation site 338-341   KGKK

[8] PDOC00359 PS00375 UDPGT
UDP-glycosyltransferases signature 354-397   WIPQNDLLGHPKTKAFITHGGMNGIYEAIYHGVPMVGVPIFGDQ

[9] PDOC00804 PS01047 HMA
Heavy-metal-associated domain 12-41    LLQLFCVGCGFCGKVLVWPCDMSHWLNVKV
```

Membrane spanning structure and domains:

| Helix | Begin | End | Score | Certainty |
|---|---|---|---|---|
| 1 | 5 | 25 | 1.802 | Certain |
| 2 | 157 | 177 | 0.765 | Putative |
| 3 | 181 | 201 | 0.779 | Putative |
| 4 | 377 | 397 | 0.735 | Putative |
| 5 | 491 | 511 | 1.931 | Certain |

FIGURE 2B

BLAST Alignment to Top Hit:
```
>CRA|147000022596013 /altid=gi|10438148 /def=dbj|BAB15179.1|
        (AK025587) unnamed protein product [Homo sapiens]
        /org=Homo sapiens /taxon=9606 /dataset=nraa /length=449
        Length = 449

Score =  931 bits (2381), Expect = 0.0
 Identities = 448/449 (99%), Positives = 448/449 (99%)

Query:  79  MPQDRTEENEIFVDLALNVLPGLSTWQSVIKLNDFFVEIRGTLKMMCESFIYNQTLMKKL  138
            MPQDRTEENEIFVDLALNVLPGLSTWQSVIKLNDFFVEIRGTLKMMCESFIYNQTLMKKL
Sbjct:   1  MPQDRTEENEIFVDLALNVLPGLSTWQSVIKLNDFFVEIRGTLKMMCESFIYNQTLMKKL   60

Query: 139  QETNYDVMLIDPVIPCGDLMAELLAVPFVLTLRISVGGNMERSCGKLPAPLSYVPVPMTG  198
            QETNYDVMLIDPVIPCGDLMAELLAVPFVLTLRISVGGNMERSCGKLPAPLSYVPVPMTG
Sbjct:  61  QETNYDVMLIDPVIPCGDLMAELLAVPFVLTLRISVGGNMERSCGKLPAPLSYVPVPMTG  120

Query: 199  LTDRMTFLERVKNSMLSVLFHFWIQDYDYHFWEEFYSKALGRPTTLCETVGKAEIWLIRT  258
            LTDRMTFLERVKNSMLSVLFHFWIQDYDYHFWEEFYSKALGRPTTLCETVGKAEIWLIRT
Sbjct: 121  LTDRMTFLERVKNSMLSVLFHFWIQDYDYHFWEEFYSKALGRPTTLCETVGKAEIWLIRT  180

Query: 259  YWDFEFPQPYQPNFEFVGGLHCKPAKALPKEMENFVQSSGEDGIVVFSLGSLFQNVTEEK  318
            YWDFEFPQPYQPNFEFVGGLHCKPAKALPKEMENFVQSSGEDGIVVFSLGSLFQNVTEEK
Sbjct: 181  YWDFEFPQPYQPNFEFVGGLHCKPAKALPKEMENFVQSSGEDGIVVFSLGSLFQNVTEEK  240

Query: 319  ANIIASALAQIPQKVLWRYKGKKPSTLGANTRLYDWIPQNDLLGHPKTKAFITHGGMNGI  378
            ANIIASALAQIPQKVLWRYKGKKPSTLGANTRLYDWIPQNDLLGHPKTKAFITHGGMNGI
Sbjct: 241  ANIIASALAQIPQKVLWRYKGKKPSTLGANTRLYDWIPQNDLLGHPKTKAFITHGGMNGI  300

Query: 379  YEAIYHGVPMVGVPIFGDQLDNIAHMKAKGAAVEINFKTMTSEDLLRALRTVITDSSYKE  438
            YEAIYHGVPMVGVPIFGDQLDNIAHMKAKGAAVEINFKTMTSEDLLRALRTVITDSSYKE
Sbjct: 301  YEAIYHGVPMVGVPIFGDQLDNIAHMKAKGAAVEINFKTMTSEDLLRALRTVITDSSYKE  360

Query: 439  NAMRLSRIHHDQPVKPLDRAVFWIEFVMRHKGAKHLRSAAHDLTWFQHYSIDVIGFLLTC  498
            NAMRLSRIHHDQPVKPLDRAVFWIEFVMRHKGAKHLRSAAHDLTWFQHYSIDVIGFLL C
Sbjct: 361  NAMRLSRIHHDQPVKPLDRAVFWIEFVMRHKGAKHLRSAAHDLTWFQHYSIDVIGFLLAC  420

Query: 499  VATAIFLFTKCFLFSCQKFNKTRKIEKRE  527   (residues 79-527 of SEQ ID NO:2)
            VATAIFLFTKCFLFSCQKFNKTRKIEKRE
Sbjct: 421  VATAIFLFTKCFLFSCQKFNKTRKIEKRE  449   (SEQ ID NO:4)

>CRA|1000682322899 /altid=gi|5802604 /def=gb|AAD51732.1| (AF175221)
        UDP glucuronosyltransferase UGT2A3 [Cavia porcellus]
        /org=Cavia porcellus /taxon=10141 /dataset=nraa
        /length=530
        Length = 530

Score =  795 bits (2030), Expect = 0.0
 Identities = 377/530 (71%), Positives = 435/530 (81%), Gaps = 3/530 (0%)

Query:   1  MRSDKSALVFLLLQLFCVGCGFCGKVLVWPCDMSHWLNVKVILEELIVRGHEVTVLTHSK   60
            M   K A   LLL L C G GFCGKVLVWPC+MSHWLN+K +LEEL+ RGHEVTVLT S
Sbjct:   1  MAPGKLASAVLLLLLCCAGSGFCGKVLVWPCEMSHWLNLKTLLEELVKRGHEVTVLTLSN   60

Query:  61  PSLIDYRKPSALKFEVVHMPQDRTEENEI---FVDLALNVLPGLSTWQSVIKLNDFFVEI  117
              IDY +   A  FEV+ +P D+      I  F++LA+NV+P +  WQS   L  FFV+I
Sbjct:  61  NLFIDYNRHPAFNFEVIPVPTDKNMSENILNEFIELAVNVMPTMPLWQSGKLLQQFFVQI  120
```

FIGURE 2C

```
Query:  118 RGTLKMMCESFIYNQTLMKKLQETNYDVMLIDPVIPCGDLMAELLAVPFVLTLRISVGGN 177
             L + C + +YNQ+LMKKL+++ YDV++ DPVIPCG+L+AE+L VPFV  L+ S+G
Sbjct:  121 TEDLGLNCRNTVYNQSLMKKLRDSKYDVLVTDPVIPCGELVAEMLGVPFVNMLKFSMGHT 180

Query:  178 MERSCGKLPAPLSYVPVPMTGLTDRMTFLERVKNSMLSVLFHFWIQDYDYHFWEEFYSKA 237
             +E+ CG+LPAP SYVPVP+ GLT RMTF+ERVKN + SVLF FWIQ YDY FW++FYS+A
Sbjct:  181 IEKYCGQLPAPPSYVPVPLGGLTTRMTFMERVKNMVFSVLFDFWIQQYDYKFWDQFYSEA 240

Query:  238 LGRPTTLCETVGKAEIWLIRTYWDFEFPQPYQPNFEFVGGLHCKPAKALPKEMENFVQSS 297
             LGRPTTLCE +GKAEIWLIRTYWDFEFP+PY PNFEFVGGLHCKPAK LPKEME FVQSS
Sbjct:  241 LGRPTTLCEIMGKAEIWLIRTYWDFEFPRPYLPNFEFVGGLHCKPAKPLPKEMEEFVQSS 300

Query:  298 GEDGIVVFSLGSLFQNVTEEKANIIASALAQIPQKVLWRYKGKKPSTLGANTRLYDWIPQ 357
             GEDG+VVFSLGS+ +N+TEEKAN+IASALAQIPQKVLWRYKGKKP+TLG NTRL+DWIPQ
Sbjct:  301 GEDGVVVFSLGSMVKNLTEEKANLIASALAQIPQKVLWRYKGKKPATLGPNTRLFDWIPQ 360

Query:  358 NDLLGHPKTKAFITHGGMNGIYEAIYHGVPMVGVPIFGDQLDNIAHMKAKGAAVEINFKT 417
             NDLLGHPKTKAFITHGG NGIYEAIYHGVPMVG+PIF DQ DN+A MKAKGAAVE+N  T
Sbjct:  361 NDLLGHPKTKAFITHGGSNGIYEAIYHGVPMVGMPIFSDQPDNLAGMKAKGAAVEVNMNT 420

Query:  418 MTSEDLLRALRTVITDSSYKENAMRLSRIHHDQPVKPLDRAVFWIEFVMRHKGAKHLRSA 477
             MTS DLL ALRTVI D +YKENAM+LSRIHHDQPVKPLDRA FW+EFVM HKGAKHLR A
Sbjct:  421 MTSADLLGALRTVINDPTYKENAMKLSRIHHDQPVKPLDRAAFWVEFVMHHKGAKHLRVA 480

Query:  478 AHDLTWFQHYSIDVIGFLLTCVATAIFLFTKCFLFSCQKFNKTRKIEKRE 527     (residues 1-
527 of SEQ ID NO:2)
             AHDL+WFQ++S+DVIGFLL CVA+AI L TKC LFS Q F K  K+E
Sbjct:  481 AHDLSWFQYHSLDVIGFLLACVASAILLVTKCCLFSFQNFIKIGKRIKKE 530     (SEQ ID NO:5)
```

Hmmer search results (Pfam):

| Model | Description | Score | E-value | N |
|---|---|---|---|---|
| PF00201 | UDP-glucoronosyl and UDP-glucosyl transferas | 962.0 | 1.5e-285 | 1 |

Parsed for domains:

| Model | Domain | seq-f | seq-t | hmm-f | hmm-t | score | E-value |
|---|---|---|---|---|---|---|---|
| PF00201 | 1/1 | 24 | 525 .. | 1 | 507 [] | 962.0 | 1.5e-285 |

FIGURE 2D

```
   1 TTCTAGAGGG TTGGAACAAC TTTTCCCTGA TACATTGCAT TTTTTTGATA
  51 CCTTCAGTAC ATGTTAAACT GGCAACCACC AGTGAACTTT ACTCTTAAAA
 101 TATTAATTTT TAACTTCTGT GCTTATATTG TCATTTCAAC TCCTTGCTTA
 151 GTAACTACAA AACCATTGCA GATCAGTGTG TGAGGGAACT GCCATCATGA
 201 GGTCTGACAA GTCAGCTTTG GTATTTCTGC TCCTGCAGCT CTTCTGTGTT
 251 GGCTGTGGAT TCTGTGGGAA AGTCCTGGTG TGGCCCTGTG ACATGAGCCA
 301 TTGGCTTAAT GTCAAGGTCA TTCTAGAAGA GCTCATAGTG AGAGGCCATG
 351 AGGTAACAGT ATTGACTCAC TCAAAGCCTT CGTTAATTGA CTACAGGAAG
 401 CCTTCTGCAT TGAAATTTGA GGTGGTCCAT ATGCCACAGG ACAGAACAGA
 451 AGAAAATGAA ATATTTGTTG ACCTAGCTCT GAATGTCTTG CCAGGCTTAT
 501 CAACCTGGCA ATCAGTTATA AAATTAAATG ATTTTTTTGT TGAAATAAGA
 551 GGAACTTTAA AAATGATGTG TGAGAGCTTT ATCTACAATC AGACACTTAT
 601 GAAGAAGCTA CAGGAAACCA ACTACGATGT AACGCTTATA GACCCTGTGA
 651 TTCCCCGTGG AGACCTGATG GCTGAGTTGC TTCCAGTCCC TTTTGTGCTC
 701 ACACTTAGAA CTTCTCTAAG AGGCAATATG GAGCGAAGCT GTGGGAAACT
 751 TCCAGCTCCA CTTTCCTATG TACCTGTGCC TATGACAGGA CTAACAGACA
 801 GAATGACCTT TCTGGAAAGA GTAAAAAATT CAATGCTTTC AGTTTTGTTC
 851 CACTTCTGGA TTCAGGATTA CGACTATCAT TTTTGGGAAG AGTTTTATAG
 901 TAAGGCATTA GGTAAGACAC TTTTGTTTTA TTTTTAATTT AGTTATCAAA
 951 AGAAATATTT TTAAAAATTG TCATACATTG TCTATGACAT ATATATGCAG
1001 GTCAATGAGT TTTTTTAGAA AATGTTGTAG CTGTTTTTCA TAAAGAAAGT
1051 GTATTTGTTC TAAGCGTAAG ATAACCTACT TTCTTAATAC CAGTAATATA
1101 CTTAAAAATG ATCATCAATA ACTAAGAGAT TATATTTGT ATTTCCTCCA
1151 AATAGCGCAA ATCAACATCA CATATTTTTG AGAATCACTG ATTGTTAGTC
1201 TGAATGTTAT AGAATTTCTA TTGAAATAAA ATGCTAATCA TTATTTTCTC
1251 TCTCATCATG TATTTAAGAA AATCTTCAGA AGGTCTTCTT TGAATTAATT
1301 TTTCAAGAGT CATTAAATTG AACATTTTCT AGAATTCTTT AATTTCTTAG
1351 GTGATTACTT CACAAAAACT TGAAAAAATA TTATAAAAAG TTAAAAAACT
1401 TACGGTCTTG TGGGGCATAA GATAGTAGAA TTTTTACTTT ACTGATATAC
1451 ACCTATTTGA CTTATTTTTA TTTCTTTGCT TTACTGATAA AAAGTTGTTT
1501 TGCTTTGCAA TTTTCATATA GTTGTGATCA GAGCTGGTCA ATGCAAGACA
1551 TGTTTTTATC CAAATATGTT TGAGAATTAT GTAGAAACAT GAAAAAAGGT
1601 ACAATTATAT CCGACACTAA AATATTGTTT AATGTATTCC AACGAATTCT
1651 TATGCATAGA CTGTTTCACA GAACTAATAT TCAGAGGATC CCAGTTCAAA
1701 TGTCCTTAGC CTTAGACATG ATTTGAATTT ACATATATTG ATTTGCTTTA
1751 AATAATTTTC CATTCAGTAA GCTGTGCCTA GCTGCAGATA GCCTACCAGG
1801 CTTTATGGAT CTAGGTAAAC AATACAAATC TCTTGGCCTC AAGTCTACAT
1851 TCAGATATTA ATTTAAAGGG GTACAGCTAT ATAGAGGTCA CTGGCAAATT
1901 TTGGTAAAAT AGGATTATAG TAAAAGCCCC CTGACAAGAT TGAAATTTAA
1951 AATAAAACAA AAGTGTTATC AAAGGGGTGA AAGAGCATTT TCCAATAAAC
2001 AAAAGTGGGT TCTGGCCATG CATTCAGAAA TTCCCCAACA ATTCTTTAAA
2051 AATCATGGAG CAGCTTGATA TATAAGAAAT TCATTTAATA ACTATATTTA
2101 TTATGTAGCT CCAACTTACT AAATTATTGA TTATTATATA TTTTATAGAA
2151 TTATCTATTG TGAGTCTAAA TCAAGAGTAT ATATTCAAAC AACTATAGGA
2201 AAAGGGATAT CAGTCAATTT CAATTCAAGG ATTTATTTCC ATAAGTGCTT
2251 ACGCACAGGT GTATTTCATT TTATTATACA TTGCTTTATT GTCCTTCACA
2301 AAAATTGCAA TTTACAAATT AAAGGTTTTT GAAAACCTTG AATCAAGCTA
2351 ATCAATTTGG CGTAATATTT CCAACAACAA GTGTGTACTT TTGACTCTAT
2401 CACATATTGG CATTTATCAT GCTTTTCAA ATTTTTCATT GTTATATCTG
2451 TTACGGTGAT CTGGGATCAG TGTTCCTTGA TGGTTACACG TTTATTAGCT
2501 TGGGGGCACC TTGATGTGTT ACAATATAAG ACAGCAAACT TAATTATAAA
2551 TGTTGTGCAT GTACTAACTG CTCCGCTGAT TCGTTTCCCC ATCCCACTTC
2601 TTCTTAGGCC TCCCTATTCC CTGAGACACA GTAATATAAC ATACAATGAC
2651 TTCTAAATGT TCCAGTGAAA AGAAAGTAG CAGGTCTCTC AATTTAAACC
2701 AAAAATATAA AGGAATAAGT TTAATGAGTA CTATAGTTTA GATATGGTTT
2751 GCTTGACCCT ACAAAATCCT GTGTTGAAAT TGATCACCA ATATTGGAGG
2801 TGGGGCTTGA TGGGAAGTGT TAGGGTCATG AGGGTAGATT CCTTATGAGT
2851 ACATTAATGC TCTCCCTGGG GAAATGGGTG AGTTCGTTCT CACTCTATTA
```

FIGURE 3A

```
2901 GGTCCCAGGA GAGATAATTA TTAAAAAGAG CCAGGAACAT CCACCTTCTT
2951 TCTCTTGCAT ATCTCTCATT ATCTGATCCC TGCACTTGCT GGCTCCCAAC
3001 ATCTTCTTCA ATGAGTGGAG GAAACCAGAG GTCTTCACCA GACACAGATG
3051 TTGGTGCCAT GCCTCTTGTA TACCCTGAAG AATTGTGAGC CAAATAAAAA
3101 CCTTTTTCTT TTACAAATTA GACAGCCTCA GTTATTCCTT TGTAGCAACA
3151 AAAAAAGCCT GGGACAGGCC AAAAACTACA CCATTGCACC AAACAGTTAA
3201 ACAAGATGTG AGTGCAAAGG AAAAGTTTTT GGAGGAAATT AAAAGTGCTA
3251 CTCCAGTGTA CATACAAATG ATAAGAACAA ATAACCATTA TCAGTGCTGA
3301 TATGGAGAAA ATTTTAGTTG TCTGGAGAGA AAATCAAATT AGCTAGCCAG
3351 CTGCAGTGAT TCATATCTGT AATCCCAGTA ACTTGGGAGG CTCAGGTGGG
3401 AGAACGGCTT GAGCCCAGAA GTTTGAAGTC CAAGGCTGCA GTGAGCTATG
3451 ATTGCTCCAC TGCACTCCAA CCTAGGTGAT AGAGCAAAAC CACTACCAAA
3501 AAAAAAAAAA AAAAAAGAA GAAAAGAAA AGAAAAAAAA TTAAACCAAC
3551 CACAACATCA CCTTAGGTTT TGGCATTAGC TAAAAACTAA TACATAGTAA
3601 AGCGTTAACT ATTCAATTGC ATGAAACCTC AGAGAGGAGA GGAAGATGCA
3651 GAAAAAAGA CTGAAGCTAG TAGAGGTTGA CTAATGAGGT TTACAGGAAT
3701 AAACTGCCTA CATGATGCAA AAGTTCAATG TGAAGCAATA GGAAGTCATG
3751 CAGAAGACTT AGCTAATATA CTCAGTAAAT GTGGCTACAG TAAACAAATG
3801 ATTTTCAATG TAGACCTAAC AGCCTTCTGT TGGAAGAAGA TGCCATTTAA
3851 AACTTTCATA GCTAGAGAAG AGAAGTCAAT GCTTGTCTCT GAAGCTACAA
3901 AAAACAGGCT GAATCTCTTG TAGTGGCTAA TGCAGCTGAT GACAAAGGTA
3951 AAGCCAATGC CCATTTACTT TTTGTAATAA TTATAGAGGA CTCTTAATAA
4001 TTATGTTAAA TCTACTTTGC CTGTGTTATA TCAATGGAAC AACAAAGCCT
4051 GGATGATATC ACATTGGTAT ATGACATGGC TTATTGAATA TTTTAAGCAC
4101 ACTGTTGAGA CCTATTGCTC AAAAAGAGG ATTCCTTTCA AAATATTGCT
4151 GCTCATTGAC AATTCACATG GTCAACAAAG GGCTCTGATT AAGATGTACA
4201 GATATTAATG TTTGCCTGCT TGCTATTATT ACATCCATCT TACATGCCAT
4251 GGATCATATA GCCTTGACTT TCAAGTCTTA TGTAAGAAAT ATATTTTGTA
4301 AGGCTATAGC TCTTACTAAT GGGGAAAGTA TATTGAAAAC CTTTTCAAAA
4351 GGATTTTTCA TTCTAGATTC CATTAAGAAC ATTCATGGTT CATGAGAGGA
4401 AGTCAAGATA TTAACATTAA CAAGAGTTTG GAAAAATTT GATTCTAACT
4451 CTCCTGGATG ATTTTGAGGG ATTGAAGACA TCATGTGAAG AATTAACTGG
4501 GGATGGGGTG GTCATGAAAA AATAAATAGA ATTATAAGTG GGCCTGAAGG
4551 TTTGTCTAAA TTGCTATAAT ATCATGATAA AACTAAAACC TGTAAAACCG
4601 GTGAGGAGGT GCTTTTAAA CAGTTACTTT TTATAGATGA ACACAGAAAT
4651 TGGTTTTGTG AGTTGGAATC TTCTCCGAGT GAAAATGCTA TGAACATTGT
4701 TGAAATGGCT ACAAATGACT TAGAATATTA CACAAAATTA GTAGATAAGG
4751 CAGCATCAAG GTTTGAGAGA ATGGACTCAA ATTTTGAAAG AAATTCTACT
4801 ATGGGTAAAC TGCTGTGAAA CATCATCATA TGCTACAGAG AAATCTTTCA
4851 TGAAAAGATG AGTCAATTCA TGCAACAATC TTTGTTGTCT AATTTTAAAA
4901 ATTGTCCAGC TGCCCTGATC AATCAACAGT AATCAGCACT GAGGCAAGAC
4951 CCTACACCAG AAAAAATAAA AATAAAAAAC CTCACTTGCT GAAGACTCAG
5001 CTTATTATTA GCACTTTTA GCCATACTTT TAACTAAGGT ATGTGCATTC
5051 CTTTTTAAAC GTGATGATAT TGCACAGCTA ATAGCCTACA AGGTATGGTT
5101 AACATAACTT TTATATGTCC TGGGACCCAA ATTTGTGTGA ATCACTTTAT
5151 TGACATATTC CTTTTATTGA GATGAACTGC AACTTATCTT GCAATATCTC
5201 CAAGATATGT GTGTATGGCA TTTCAAATAA GATGTGAAAT TATTTTATTA
5251 GTATAAAAAG CAAATTTAAT TTTCTTTCCT TTGATCATCT TTATCCTTGT
5301 TACTGTGTAT TTATCCTTTA AACATTGAAT GACTCCAATT GTTTAAAACT
5351 GAGTCTTTCT TAAATGAGTC CTAATATCAT AGTAATTAAA ATCACCTACA
5401 AGTTGGTAAT GCAGGCAGCA TGTGAGGCAC AGAAACAAC AAATTTATAA
5451 GACATAAATG CATTTGCTTG GAAGCTGAGA GAAGGCTCTA TTCTAATTTC
5501 TGATAACTTC AAACTGAGTA TCTTCAGTAA AATTTATTCA CTATCAAATT
5551 CAAGGCGTTT GGATTTATGA CCTAGGAAAA AACTTCAAAC ATTAAAATGT
5601 GATGACCTTA AAAAGAGGCT CTCCACACTA TGGTGTATAA CACCACCAAC
5651 TTTGATTAGA ATTTTAAAGA GAAACAAATT CTCTTATGGA GTTTATCTTT
5701 TTATCACTTG CAAAATATGT TTTTGTAAAG AGATACTAAT TACTTAGTTA
5751 TTTGTAGTTA GCCATTCTTC TGATTAAAAA CCTAAAATTA AATCTTGAAA
```

FIGURE 3B

```
5801 ATGTGTTTTC CTTCAAAACA CATCATTTGA GAGAAACACT AAAGTAAGTG
5851 TATGATTATC ATAGCATGTA CATAGGTGCT TCACAACCCA AAAAGAATAT
5901 TGTCATGGGT AAGAATCAGT AAAGGAATTT CTCCTAATAA AACAGTAGCC
5951 TATTAATTAA AGTAATGATA TGCAATACAG CAAGTTAAAG GGAACTGATC
6001 CTGGTGGGAT TATTGAAAGA TATACCCTTG ACTATAGATT AGAAAATACA
6051 GAGATGTTAT TTAGTGAAGA TATTGTGGTA CTCATTTATC ATCTGCAATT
6101 CACTTGCAGA GGAAAAAATG AGTAATAAAT TCATTTGCAT TTTGGATTTG
6151 TGTCTTTAAG TTGTGAAAAT ACACTTAAAT ATAACCATCT GTCCTTTGCT
6201 CCTTCCTTCC TTCCTTCTTT CCTTCCTTCC TTCCTTCTTT CCATCCTTCC
6251 CTCCCTCCAT CCTTCCTTCC TTCCTTTCTT CCTTCCCTCC TTTCTTTCTC
6301 TGTCCTTCCT TCTTTTTTCC TTTCTTTCTT TTTTCTTCTT TATTATTTCA
6351 TTAATTCCCC CTTCCATTTG ACGTCTAAAA GCCATGTTGT TCTAGAGGAC
6401 TTAAACTTAT TTTTTTCTTA ATAGCTTACT GAAAATTAG TGATACAATT
6451 TTTTATTTGA ATTGTATGCT AATTCATTCT GTTATTTCTT TTATTGAGGA
6501 AGGCCCACTA CATTATGTGA GACTGTGGGA AAAGCTGAGA TATGGCTAAT
6551 ACGAACATAT TGGGATTTTG AATTTCCTCA ACCATACCAA CCTAACTTTG
6601 AGTTTGTTGG AGGATTGCAC TGTAAACCTG CCAAAGCTTT GCCTAAGGTA
6651 GGACTATTGT ATTAAGGAAT ATTATGTACT TTATGACATG ACTTGTTTTC
6701 CCTTGAAAGA TTACAACCTT AGTTATAGAA GGATGATGTT GAATGTCGTC
6751 TGTTTGCAGC TCCATATTTA TTTTCCATGC CACAGGGGCT CTTATAGGTG
6801 ATTATATGTC TTTTCGGTAT TATATTGAGA AAGTAGGCAG AAGAATTTCA
6851 TGATTAGAAT AGATTTTAAA ATACTAGTAT TACAATAGTT TGGATAATAA
6901 ATTGAATTAA TAGGGAATTG GAGCCATGAA GATCACTAAA AAGAATGCTC
6951 TAGCCTTTCT CACAATCAAA TTGGGCTTAT GAACAAGGAT ATTTGTCATG
7001 ATAGTACAGA AATAAGCATA TTTTCATGAG ACATATTGGA TATATTCCAC
7051 AGGAGTTGGT GAGTGAGAGA AAATAAGTGA TGAAGGAAGA CAAAGAATAA
7101 AAGAAAATTT CAATAAATGG AAAGTTTAAG TGTTTAATGA TAGTGATGAC
7151 TTTTACTCAA ATAAGTGCTT AGAAGTCATC TTGTTTGTGA TTTATATGAT
7201 GAATTCTGTG TTGTGACTAT CCACTTTGAG CTCGTGAGAA TGTTAGGTGA
7251 GGTTTAATAA AAGCCATTTG AGAAAACAA GGTTTCAACC TCTGTGGACA
7301 GAAATCTAAA TATCGATAGT TATCAGGACA AAGTAGAGCT CATAGAAATA
7351 ATTTTGCAGC CTGCAGGTTT GTTTTGGAGT GAAAATAAAA TTGTATACTA
7401 TATTCCTAAA TCATCAGAGG AAAAAATTTA TAGTTCAAGG AATGTTGAAA
7451 GAAACAATAT TGAGAAGTAA AAGTGAGTAA TAGTTGTTAT AGTTTTTAA
7501 TAGTTTTGTA AGTATGTCTT GAGTTCACTG TCCCAAAAGT GGCTATTAGC
7551 TCTAGCCTTG ACCTGACAAG GTTCTAGGAT ATTTAGTCAT GGATGTTCAT
7601 AATCTACCTC TTACGGGATA CTTTTTATTC TGATGAACAG CCTAATGCCT
7651 AAGTGTGCAA TCTATACCAA GATTGTTCTT ATAGGGAACT TGTTTACACT
7701 GGAAGACACC ACTGTGTCTC TTGTATGACC TATGTCTTCT TTATCCCTAC
7751 AAAGGTAACC ACATTATAGG AAACCCTGAC AAGGCCAGAT GTTATATTTG
7801 TGTTGGTCAA GTGAGAAAAC ATGGGAGAAA CTTAACCAAA CACATAAAAT
7851 AACAGAAACA GTCTTCTTTG ACCATTTCTA GAGAAAAGAG TTCAGCATCC
7901 CTTGTAAGGC CACTAGGAAG AAGAAAATTC TCTGGGAAAA GCACATTCAA
7951 CCAATGAATG GAGACCAAGA AAGAGAGTGA GGGATCTATG TGCCAAAATG
8001 TTAACTGGGA TCCAGGGTGT TACCTAGGTG GGTTTCCAAT GGGGAACTGT
8051 AATTGGTAGG TTTAATGCAA GCAGGCACAA AGTCCATGGA GGCATTCTGA
8101 GACTGAAAGA TAGTCACTTT GGCATATCTG CACAGAATCT GATCAGTGAT
8151 TCAAGCCCAA GTAGGCTGTA TCTAGTTGTC CTATAGGGTG GTTACCAGGA
8201 GGCAGTGTGT AAGTAAAAAT CCTGACTGAA CACATTGAGG AAATGGAAGG
8251 AGGTGGAAGA TTTTAAACGG TGTCAGTGTT GACTAAGACC TGCTTCTGGT
8301 ATGGAAAATT CAACTTATAT TTTAAATGCA TAGCCAGACA ACATAAAATT
8351 ATAAGAATTT ACCACAATAG CTATGGTAAC AATACTGGGT TTACCTATTA
8401 CTACAGAGTG AAAAGAAAAC CCTCATTTCC CATTTTATGG AAATATAATC
8451 AAAATCCTAT AAGGAAGGTT TCAGAGCCAG TAGGATTTCC AGAAAAATTA
8501 TTGGTTTTAT AGTAAGATGT GTATTGATGA ATATAATTTT ATTTATTAAT
8551 TATTAATATC ACTTTACTTA CCAGGAAAGT TATACCAGAA AACCAAGCTC
8601 TCTTAAGCCA TGGCATCTGT ATCTAAAATA GAAATACAGA AGGAGAGCTG
8651 ACAATTTCCA TCATTCTCTA GGTAATCTCC CATGCCATTC TACCCTTTAT
```

FIGURE 3C

```
 8701 TCCCACACTC CCAGTTTTAC ACACACACAC AAACACACAC ACACAAACAC
 8751 ACACTCATAG AAATAATCAT AGAAGACATA TTTTTAAAAA AGTTAGATCC
 8801 ATACAGTAAT AATTTATTAG GTAAAAGCTT TTGTGCTGAT AATTTTACAA
 8851 GTTTAATTGA GATATATTTT AGGGCTGTCT TACACTAAAT ATTTATTTTT
 8901 ATTTTTTAAA TTTGACATGT AATAATTGCA CATGTTTAAG AGAAATGCTG
 8951 TGGTATTACA ATACATTTAA ATGTTGTGTA ATAATTACAT CAAGATAATA
 9001 AACCCATCAT CTAAATATTT ATCATTTCTT TGTGGTGATA ACATTCAAAA
 9051 ACCTCCTTTC TGGCTATCTT GAAATATGTA ATACATTACT ATTAACTATA
 9101 GTTACCCAAC AACTTAATAT AATAACAGAA CATATTCTTC CAAATTTAAA
 9151 CGTTGTATCC ATTGATCCAC CATTTCTCAT TGCCCTCCCT ACTATCTCTT
 9201 CAGCCTCTAG TAACCACAAT TCTACTCTCT AATTATATTA TGAATGCATT
 9251 TTTTGATTCC ACATATAAGG GATACCATGC TATCTCTGCC TGGATTATTT
 9301 CAGTTAACAT TATGCCCTGG AGGTTCATTC ATGTTTCTAC AAATGACAGG
 9351 ATTTCATTCT TTTTTTTCCA ATATATATTT AATGAAATGG ATATATATAA
 9401 ACATTGGAAA ATGTATATAT ATATATATAT CTCCAGTGGA ATGCTATTGA
 9451 GCTATAAAAA AGTTAATATA TAATAGAAAT AAAGCTTATA TATATCTAAT
 9501 GGAATGGATA TATATATATA ATGGAATAGA AATATATATC TATACATATA
 9551 AACACACGCA ATATACATAT CCATTTCATT GCATATATAT ATATATAGAG
 9601 AGAGAGAGAG AGAGATATTT TCAAATGTGT GTATATATAT CCAATGGAAT
 9651 GGACATATAT ATATGTATAT TTTTTCCATA TTTTCTTTAT GTATTTCTTC
 9701 ATTAATGGAT GTTTAGGTTG ATTCATCCCT TGGGTATATG AATAATGTTG
 9751 ATGTAAACAT AGAAGGACAG ATATCTCTAT GACTTCTTAG TTTATTTAAA
 9801 TATACACCCA GTAATGGAAA TGCTGTATAA TATGGTAGTT CTATTTTCAT
 9851 TTTTTGAGGA ACTACCATAC CGTTTTCCTT ACTAATTGTA CTAATTTGCA
 9901 TTTCCCTCAA CAGTTTATAA AAGATCTTCT TTCTCTGCAT ACTTTCTAGC
 9951 ACTTGTTATT TTTGCCTTTT GATAATAGCC ATAACAGGGG TGATGTGATA
10001 TCTCATTGTA GTTTTGATTT GCATTTCCCT GATGATTAGT GATTTTGAGC
10051 ATTTTGTAAT TATACTTCTT AGTCACTGAT AGTCTTCTTT TGAGAAGTGT
10101 CTATTCAGGT CTTTTGCTTA TTTTTTAATC AAATTAGTAA TTTATTTTTA
10151 TTGACTGATG TGACTTCTAT GTATATTTGA GATAGTAACT TATTGTCAGA
10201 TTCATAGTTT GCAAATATTT TTCATGTTGT GAATTGTCTC TTCACCCTGT
10251 TGTTTGCTTC ATTTCTCTG CACAAGCTCA ATGCTTTGAT ATAACCCATT
10301 TATCTACTTT TCCTTTTGTT GGCTGTGCTT CTGAAGTCCT ATCCAAAAAA
10351 ATCCTTGCCT AGACCAATGT CACAAATCAT TCCTCCTACA GTTCTTCTA
10401 GTAGTTGTAT AATGTTTGGC CTTATATTTA ACTTTGTAAT TCATTTTTAC
10451 TTACTTTGTA TATGGTGAGG GATAGAGGTC TAGTTTCATT TTCTGCATGT
10501 GGATATGCAG TTTTCCTAGC ACCATTAGT GAAGAGGTTG CCTTTTTTCT
10551 ATTATGTGTT CTTGGCACCT TTGTCAAAAG TCAGTTAGCT GCTATATTCC
10601 TCCATTTGTG TTGTTATAGA GGAACACATG AGACTAGCAA ATTTATATAT
10651 CAAATAGAAT TATTTGAATG ATAGTTCTGC ATACTGTACA AGAAGCACAG
10701 CACTGACTTC TGCTTGGCCT CTGGTAAGGT TCTCAAGATG CTTCCACTTG
10751 TGGTAGAAGG CAAACATGAG CTGGTATATG CAAAGGTCTC ATGACAAGAG
10801 AGGAAACCAT AAAGAGGGGA TGTGAGGGAG TGCCAGGTTT TGTAAAACAA
10851 CTAGCTCTTC TGGGAACTAA TAGAGTAAAA ATTCGCCTCC CAGGCAGGGG
10901 ATTAATCTAT TCATGAGGGA TCTGCTTCCA TGACAAAGGC ACATTCTGTT
10951 AGATTCTACC CCCAATATTG GGGATCAAAT TTTAACATGA AGTGTGGAGG
11001 GCTCAAATAT CCATACTATG GCAGCAGTAA ATGCATAAAT TTATTTTGTG
11051 GATCTCTATT CTATATAGTA TTGGTGTATG TATCTGTTTT CATGCCACTG
11101 CCATACTGTT TTGGTGATGA TATCTATGCT ATATATGTGT GTGTGTATAT
11151 ATATATTATA TATATGTATA TATGTGTATA TTATATATAT GTATATATGT
11201 GTATATTATA TATATATAAT ACTTTAAGTT TTATATATAT ATAAAATACT
11251 TTAAGTTCAA GGGTACATGT GCAGGATGTG CAGGTCAGTT ACATAGGTAT
11301 ACATGTGCCA TTTTGGTTTG CTGCATGCAT CAACTCATCA TTACATTAGG
11351 TATTTCTCCT AATGCTATCC CTCCACCAGC CACCCAACCC CAACAGGCC
11401 AGGTGTGTGA TGTTCCCCGC CCTGTGTCCA TGTGTTCTCA TTGTTCACTT
11451 CCTACCTAAA AGTGAGAACA TGCAGTGTTT GATTTTCTAT CCTTGTGATA
11501 GTTTGCTGAG AATGACTGTT TTCAGCTTCA TCCATGTCCC TCAAAAGGAC
11551 ATGAACTCAT CCTTATTTAT GGCTGCATAG TATTCCATGG TGTATATGTG
```

FIGURE 3D

```
11601 CTACGTTTTC TTAATCCAGT CTATCACTGT TGGACATTTG GGTTGGTTCC
11651 AAGTCTTTGC TATTGTGAAT AGTGCTACAA TAACCATATG TGTGCATGTG
11701 TCTTTATAGC AACATGATTT ACTATCCTTT GTGTACATAC CCAGTAATGG
11751 GATAACTGGG TCAAATGGTA TTTCTAGTTC TAGATCCTTG AGGAATCCCC
11801 ACACTGTCTT CCACAATGGT TGAACTAATT TACATTCCCA CCAACAGTGT
11851 AAAAACGTTC CTATTTCCCC ACATCCTCTC CAGTATCTGT TGTTTCCTGA
11901 CTTTTTAATG ATGGCCATTC TAACTCACAT GAGATGGTAT CTCATTGTGG
11951 TTTTTGTTTG CATTTCTCTG ATGACCAGTG ATGATGAGCA TTTTTTCATG
12001 TGTCTTTTGG CTGCATAAAT GTCTTCTTTT GACAAGTGTC TGTTCATATC
12051 CTTTGCCCAC TTTTCAATGG AGTTGTTTGT TTTTTCCTG TAAATTTGTT
12101 TAAGTTCATT GTAGATTCTG GATATTAGCC CTTTGTCAGA TGGGTAGATT
12151 GCAAAAATTT CTCCCATTC TGTAGGTTGC CTGTTCACCC TGATGGTAGT
12201 TTCTTTTGCT GTGCAGAAGC TCTTTAGCTT AATTAGATCC CATTTGTCAA
12251 TTTCGGCTTT TGTTGCCATT GCTTTGGTG TTTTAGTCAT GAAACCCTTG
12301 CCCAGGCCTA AGTCCTCAGT GGTATAGCCT AGGTTTTCTT CTAGGATTTT
12351 TATGGTTTCA GGTCTAACAT TTAAGTCTTT AATCCATCTT AAATTAATTT
12401 TTGTATAAGA TGTAAGAAGG GATCCGTTTC AACTTTCTAC ATATGGCTAG
12451 CGTGTTTTCC CAACACCATT TATTAAATAG GGAATCCTTT CTCCATTTCT
12501 TGATTTTGTC ATATTTGTCA AACATCACAT GGTTAGAGAT GTGTAGTGTT
12551 ATCACTGAGG CCTCTTTTCT GACTCCATTG ATCTATATAT CTGTTTTGAT
12601 ACCAATACCA TGTTGTTTTC GTTACTGCAA CCTTGTAATG CAATTTGACA
12651 TTCAGGACCA TGATGCCTCC AGTCTCTTTT TTTTTTTCTA AATAATTTTT
12701 TTGTCAATGT AAGCTCATTT TCGCTTCTTT CTGATCCATA AAGTATTTTT
12751 TTCCCATTTT GTGGAGAACG CCGCNNNNNN NNNNNNNNNN NNNNNNNNNN
12801 NNNNNNNNNN NNNNNNNNNN NNNNNNNNNN NNNNGGCACA CCTCGTGCGC
12851 ATATATATAT ATATATATAT ATATACCTCT ATATATATAT ACATACATAC
12901 ATACATACAC ACCTCCTTGT CTGGTGTGGG ATCAGGGTAA TGCTAGCCTC
12951 ACAAGATGAT ACTGAAGTGT TTTTGCCTTT TTGACTTTTT GATGGTTTGG
13001 AAGAGTGAGA AAAAGTGTTA TTAATTATTC TTTAAATTTT GTTGAATTTC
13051 ATAGTGAAGA CCTTAGCTCA CTGGCTTTTT TAATGAGAAC TTTATTACTG
13101 ATTTAAACTT CTTCTTCATT ATTTATTTCT GCCTTGTTTT TATTTCTTCA
13151 TAATCCAGTC CTATTTTATG TGTCCACTAA ATTGTTTATT TTCCTAGAAT
13201 TTTTCCATTT ATTGGCATAT GCATGTCCAT AGAAGCCTTT TATAGTCCTT
13251 TTCATTTCTA GTGTCATTTT TTTCCTTTTT TTAAGAATC CTTAAGATTT
13301 TAGAGATGAA ATGTCACTTT GTTACGCATA CTGGAGTGCG GTGACATTAT
13351 TATAGCTCAC TGAAACCCAA ACTCCTGAGT TTAAGCAATC CTTCTACCTC
13401 AAAATTCCAA AATTCCTGAG TAGCTGAGAC AGGCATACAC CATCAAGACT
13451 GGCTAATTTA TTTCAAATTT TGTAGAGATG GGTTCTTACT AAGCTATTCT
13501 CAATCTTTGG GCTTCAAGTG ATTCTTCAGC CTCTGTCTCT GAAAATGCTG
13551 GGTTTATAGA TATGAGCCTC TATGCCTGAT TTGCTTTGTC TCTTTGTAAT
13601 CTCCCATTTT ATTTGTGTCT TTTCTGGTTT GTTTCATTTT GTTATGTTTT
13651 CAGTTACCTT GCTAAAGCTT TGTCGATTTT ATCTCTTCAA ACAACTAACT
13701 CAATATTTTG CTGATTTTCC ATATAGTATT TTATTTCTAT TTCATTTATT
13751 TCTGCTCTAA TCTTTGTTAA ATATCTTGTT TTCCTAATAA TTTTGAGTTT
13801 CCTTGTTCTT GTTTTCTAAT TCCTTGCGAT GTTATCATAA ATTGTTTATT
13851 TGATATCTTT CTACTTTTTT GATGTGTGTG TTCGTTGTTG TAGACTTTCC
13901 TCTTTATTAT TCTGATTTCT TCCTCAATTC TCTAATATTA TGATTGCATT
13951 ATTTTCCAAG TTTCTTTTGT TTTTTATTTT ATAGTTTATG TGATTCCTGA
14001 ACTTGTCAAA GAGATTATTG TGAATTTGAT GTCGGATATT TAAGCATTTT
14051 CAAAACTTTT GGTGCATTAT TGAAATTTTA TTGGTTTATT TTAGAGATGT
14101 CATACTTCCC AGTTTTTTTT TAACAATACT TGCTCTTTAT ATTGATGTCT
14151 ACATATTTAA AAAGATAACC ACCTGATTCA GCTTTTAAG GTGATATGCA
14201 GTGGTGTTAA GTGTGTACTG CTTAATATCA GAGCTGAATC ACTGCCCTGA
14251 GGATTCTTTC TGTTCTGAGG AGAGCTTGTA GTTAATAGCA GAACCTAAAT
14301 AGTGCAGTAG AGCTAAATCT CTTCCATGCT GTTGTTTCC TGTCTGGGGA
14351 AGACTTATCA TGACCATGAA AACATAATGC TGTGCCAGAA CTTAAACCCA
14401 AACCTGTAGT AATTTCTGAG TTGAGGAAGG CTTAAGAAAT AACTGGAACT
14451 TAGTTACTAA CCTGATAGTT GTTTCTGAGT CAGAGAAATG CTCTGCATGA
```

FIGURE 3E

```
14501 TCACCTGGGA TATTTGTAAA ATCTAACCAA AGATTCTAGC CTTCCCCTTG
14551 GATTGTGCCT CCTGTACTAC TGTAGTGCTG GCTAGGTCCT CATCAGTGAA
14601 TTCCCTGCTG ATAGGACCAC AAAGCATCTG CCAAGATCTG TTTGCCATTT
14651 GCTGTGATTA GTGCTTCTGC TCTTTGCTTC CAATTCAACT CAGGTGGTTC
14701 AGCCCTTCTG ACACTCCTAA TACCTCCTGT GGGATGGAAC ATAGAAGGCT
14751 TCTCACAATG ATTCACACAC TGATATGGAG ATTGAATGTC CAGTTGCAAC
14801 TATTTTCTTC CACCTGTGTA ATTGCAGGTA CAGGGAAGTT TTCTGTGACT
14851 GATGCTATTT TGGTTTGGAG AATGGGGTGA TGTGGCACAA TGATCTTTCT
14901 TCTTTCTGGT CATGGATTTT TTAATTTCCA TGAACCCATA AGATTTTTCA
14951 CTTTTCTTCT GAGCTCTGGT GCTTTCAGAG TGGTATTTTT ATATTCGAAT
15001 AGTTGCTAGT TGTACTTTTA AAAGCGATTG ATGCTGGAGG TCTTCTATTC
15051 CACCATCTCG CTGATGTCAG TCCTCAAATA ATAATTTAT ATTTTAGCAA
15101 ATTATTTTGG TTTTAGGATT TTGTGTCTAC GTGACACAGA CATGAAAAGA
15151 GATGTACTCA TTACTGAAAC TTTTTGCATA CTGTTTTGGT TGTGCGCCTT
15201 TTCTAGTATG AATGATTACA TATTTAAGCC ACATGTTTTA TACATAGACT
15251 GTCCTTTAAA GAGACTAGAT AGTTCTGTGT GTCAGCATAT AGGGACAGAA
15301 TATAACTACA CATTAATAAT TTCTCAAGTA TTTATTTTAG AAGTGTAAGT
15351 AACCTTTATT TTAATTTTTG TTATATTATG CCTCTGTAAT GCAGATAAAT
15401 TTTTATCTTC AGGAAATGGA AAATTTTGTC CAGAGTTCAG GGGAAGATGG
15451 TATTGTGGTG TTTTCTCTGG GGTCACTGTT TCAAAATGTT ACAGAAGAAA
15501 AGGCTAATAT CATTGCTTCA GCCCTTGCCC AGATCCCACA GAAGGTCAGT
15551 AAAACCTCCA ATCCTGATAA GCAGCTATTC ACATAATGAA ACAGTATGGT
15601 TTTATTTGGG TCTTGAATCT CATTTTCCAC TTAGCATAAC AGGTACCAAA
15651 ATTTGCAAAA CATTATAGTA GTGTACATGG GCATAACTGA TCATTTGCCT
15701 ACTGAGTCTT GCTGTTACTG GAAACAACTT TCTTGATTGT CATTTGTTTA
15751 TAATAAAATA GATATAATAA ATAAAGCTCT ACCTTATATT TTAGGATTTG
15801 AAATCTAAAA GCGTGTGCCA ATGATTCCAA AAAAAAATTC TGACATCTAT
15851 TATTTCAAAG GACCAGAAAA AGGAAACTG ATATAAAAA AAAAAGAAGA
15901 ATCAATCTCA AGAATATCTT CTCATATTTG TGTGTATAAA AACTGTATTC
15951 AGGGTAGTTT TGCTTAGAAA TAAAAGCTCA GATTAATGTA GTCTTTCTAA
16001 ATAATTAGAA GTTTCAAAAG TAAAATGTCA ATTACAATTA TAGTATAGTA
16051 ACAATTATTT AAGTAATGTA ATTATTTATG ATACTCCACT AATTTTAACT
16101 TTATTATTAC TGTAATTCTA GAATTTCACA CTTTAGATAG TGCTATATAT
16151 AAACTATCCA AAAGATATTT CATTTTATAT TTAGCTAAAA TACTTCAAAC
16201 TCAATAAAGG CAAGCATACT AATTAGGAAT TTGAAATATT GTAATTTCAA
16251 TTATGAAATT ATCTGTTAAG TAGTTTGAAA CATCTATGCC GTTCTTTGTT
16301 TTCAAATGTA TAAAATTTGT ATAGGTGTCC AACAAAGAAA AATTGTGTAA
16351 AAAAAAGGTA CAATCTCAAA GAAAATTTAT CATTGAACAG TGGAACATAA
16401 GTAATTTTCT AGCTCATTCT TCTTCAATAA AACAATTAAA TATAAGAAGA
16451 AAGAGGCCAG GAAGGAAATA GAGAAGAAAA GACACCCGAT TATCCAAAAG
16501 ACACACATAA TTGAAAGCAA ATTTTTATCT GCAGGGAACT GTAAATTTGA
16551 TGGTAGAATG AGATTGGCTC CATGAGTTAA AATGACACAC AGATCAGGTA
16601 CTTATAAAAT TTTTAATTCT TATATAAAAA TAGATTAGCC ACTGCTGAAT
16651 TATTTTTTA AATATTCACT GGTATTCTCA TTCTCAAATA TTTTTAATTG
16701 GTAATAAAAT AATAATAGCA TACCTAATAG GCAACTGGTA CACATTATTT
16751 TAAAAGATCT TTGTAAAACG TCCTACTATA TCTTTCAGTC TTTACGCGGT
16801 AGCTCTACAC ACCCCTGTCT CAACCATCAC CTGAAGTACA ATGAGTTTAT
16851 AATTTATAAC TATATCTACA TCCTTAGAAT GCTAATATCC TGTGGTTCAC
16901 TCTGTGAAAT ACATGTGTTT CTTCCGTAGG TGTTATGGAG GTACAAAGGA
16951 AAAAAACCAT CCACATTAGG AGCCAATACT CGGNNNNNNN NNNNNNNNNN
17001 NNNNNNNNNN NNNNNNNNNN NNNNNNNNNN NNNNNNNNNN NNNAAAAAAA
17051 AAGACCCAAT CCCAAAGAAA ATTTATCATA GAACAATGGA ACATAGGTAA
17101 TTCTCTAGCT CATTCGTCTT CAATAAAACA AATAAATATA AGAAGACAAA
17151 GGTCAGGAAG GAAATAGAGA AGAAAAGATA ACCGATTATC CAAAATCACA
17201 CACAAAATTG AAAGCAAATT TTATCTGTGG GGAACTGTAA ATTTGATGGT
17251 AGAACCAGAA TAGTTCCATG ATTTGAAATG ACACAGAGAT CATGTACTTA
17301 TAAAATATTT TATTCTTATA AGAAAATTGA GTAGCCAGTG CTGAATTACT
17351 TTTTAATGAT TCACTGATAT TCTCATACTC AGATATTTTA ATTGATATTA
```

FIGURE 3F

```
17401 AAATAATAAT AGTATACTTA ATAGTCAACT GGTACACATT ATTTGAAAGG
17451 ACTTTTGTAA AAAGTCCTAC TATGTCTTTT ACTGTTTACA CAGTACCTCT
17501 ACATACCCCT GTCTCAACCA ACACCTGAAG TACAATGAGT TTATAATTTA
17551 TAACTATATC TACATCCTTA GAGTGCTAAT ATCCTGTGGT TCAATCTGTG
17601 AAATACATGT GTTTCTTCCA TAGGTGTTAT AGAGATACAA TGGAAAAAAA
17651 ACCATCCACA TTAGGAACCA ATACTCGGCT GTATGATGGG ATACCCAGA
17701 ATGATCTTCT TGGTAGGTCT ATGAGAAAGT AAAAATATGA ACTAGACGAG
17751 GAAAAAATGA ATAAATGTTA AACAGCAAGC AAATTCAGCA AAGATCTAAA
17801 ATTATAAAAC TTTATTTTAC TTACTCTTTT GAAGCAGATA TAATTAAAGG
17851 ATTGACTAAA ATTGTATAGA TTCACACTTT CTATTGTTAA GGTGAGAGTG
17901 ACAGGAAATT CAGAAGGAAT TAATGCCTAT TTTTCTGGAG ATAGAAATGA
17951 TCTTTAGTAG CAATGCTCCA TGTGCTCACC TTCTAAAGAA AGTGCTGTAC
18001 GCTTCAGTGA GTTATCTCGT AATTCCCATC TGTAGTTTTT AAATAATTTT
18051 AAAAGTTTAG AATAAAATAT CTCACCATTT CTCATCCAAT TTACATACTA
18101 GGTCATCCCA AAACCAAAGC TTTTATCACT CATGGTGGAA TGAATGGGAT
18151 CTATGAAGCT ATTTACCATG GGGTCCCTAT GGTGGGAGTT CCCATATTTG
18201 GTGATCAGCT TGATAACATA GCTCACATGA AGGCCAAAGG AGCAGCTGTA
18251 GAAATAAACT TCAAAACTAT GACAAGCGAA GATTTACTGA GGGCTTTGAG
18301 AACAGTCATT ACCGATTCCT CGTAAGTACT ACTGCTTGTA CAGACTGATC
18351 TAACATTGAC TATGTTATAC ATTATACCAG AAAATGTTAA ATATCATCCT
18401 GGTAGACATG TTGAGGGATT TTACTCCACA ATATTGAGTC ATTCATCACC
18451 TTGTTACTGG AATAGTTGTG GAAATTGTAG TTCATAGAGT GTCAAACTTT
18501 CTTCATGGAA ATATTAGGTT TAAGTTAACA ACTGGCTTAC TAAGCTTTTA
18551 TTCACATCTT AATTTTACCC CATTTTGTTA AGAATATACT CTTTCAGTCT
18601 CTCCACTATA TCTGTTTAAT ACTATGTAAC CAACAATATT CATGTCACAA
18651 CCAGAATCAA TCTTTTACTG AACATGTTCT TGGCTTGCAT AACATATACT
18701 ACGGTTTATC TACGTGTCTT TTATGAAAAC AAAACTACAA CTTTCTAAGT
18751 TCTATGTGTG TTTTTCCCTT CCAGTTATAA AGAGAATGCT ATGAGATTAT
18801 CAAGAATTCA CCATGATCAA CCTGTAAAGC CCCTAGATCG AGCAGTCTTC
18851 TGGATCGAGT TTGTCATGCG CCACAAAGGA GCCAAGCACC TGCGATCAGC
18901 TGCCCATGAC CTCACCTGGT TCCAGCACTA CTCTATAGAT GTGATTGGGT
18951 TCCTGCTGAC CTGTGTGGCA ACTGCTATAT TCTTGTTCAC AAAATGTTTT
19001 TTATTTTCCT GTCAAAAATT TAATAAAACT AGAAAGATAG AAAAGAGGGA
19051 ATAGATCTTT CCAAATTCAA GAAAGACCTG ATGGGGTAAT CCTGTTAATT
19101 CCAGCCACAT AGAATTTGGT GAAAACCTTG CTATTTTCAT ATTATCTATT
19151 CTGTTATTTT ATCTTAGCTA TATAGCCTAG AATTCCACGA TCATGAGGTT
19201 GTGAGTATAT CTCATTCTTT CGTTGTATTT TCCTAGGTGT CTTTACTCTC
19251 TTCTCTCACT TTGTGACACA AGGACATGAA TACATCTAAA TTTTCCTATT
19301 TCTGATATGA CTGTTTTGAT GATGTCATTA CTTCTATAAC CTTAAGTGAT
19351 AGGGTGACAT GCAATATGAT TATTCCTGGT GTGCGCCCAA ACACATGGAT
19401 ATAAAGAGGT AAAAAACTTA AAATTCACAA AATTCAGTAA ACCACACAAA
19451 TCAGGTAAGT GTTCTATGAG ATTAGCTGGC TATGAGAAAC ATAATGATGT
19501 TTCTTTTTCA ATTTAAATAA GCCCTTCTAC ATAGCCAGCA TCAGTGATCT
19551 CAGAAAATAA ATTGCTAATA ATGATGACAT GGCATTATGC TTAGAAAAGT
19601 TTGCTGTATT TCCATAGACC TCATCTAGAT GTCATGGCCT ACATTTCTGC
19651 CATCACTCAA CCAATACTTT TTTCTGTTTT CTTGATGATA AAAAGACCTT
19701 TCTCATGATT GCCATCAAAT AACAAAAGAA ACTATTTTTT TTCTCACATA
19751 GAGAACATGT CAGTAAGATA TTCAAGGTGA ACAGATATTT TTGGGATTAG
19801 TAACTATTTG AAATATGTGG TGATAATTAC TGAGTTTATA AAATTTATTT
19851 GATAGTACAC TTAAAGAAGA TTTATATGTT TATTCTTTAA AAATGATGAA
19901 TACTCATAAT TCTTATCTCT ATAATCAAAA GTATAATTTA CTGTAGAAAA
19951 ATAAAGAGAT GCTTGTTCTG AAAGTAAGAT CAGTGAACTG CTTTTCAGTC
20001 TCAATCTTTG AGAATTGTAA ATTCATCAAA TAATTGCTTA CATAGTAAAA
20051 ATTTAAGGTA TTAGAAAACC TGCATAACAA ATAGTATTAT ATATTAAATA
20101 TTTTGATATG TAAAGCTCTA CACAAAGCTA AATATAGTGT AATAATGTTT
20151 ACACTAGTAA GCAAATATGT TAATCTTCTC ATTTTTTTAC TGTCATATAA
20201 TCTTAGTGAT ATGCCTATTA ATAGTTTTAA ATAAATAAAT TGGCTTATCT
20251 GGCTTTTTGA AAATTTTGAA ATTCTTACAG ATGTTGATTA GGTATATCTA
```

FIGURE 3G

```
20301 CAAATTAATT TCAATTTTAA AATGATGATA TAAAAATAAA TATAAGTATT
20351 TTTCTTGTGT ATGTATACAA TAAATATAAA TAAAATTGTT TACTGTTTTG
20401 AAAGTTTCTT AAGTTTTTAC ACTGATATGT TTTTTGACTT TTACAATATT
20451 ATTATAATCT AGGAAAAGCT GATTATATCT GTTTTAAGCC TCATCTTTTC
20501 TCTGTAATTA AACACAGTAA TTTATTAACA TGCTGTGACA GGTGGGAAGC
20551 CATTTCTGGA GTTGAGCCTG CTGACACTCT GGAGCTTTTT AGGTTGGACG
20601 TTCATTGTAT GTGGGACTCT CTGCCTCTCG ATAGCTGTTG CTCATAAGAC
20651 TCTCCTTCAT CAATCTGGCA TTGAATTTTG CGATCAGTTG CAATCAGAAT
20701 CCAATTGGCC TTGCCGTTTT AGTATGTTCT ATCTTAACCA GCAATTTCTA
20751 ACCAGGAGCC TGCCCAGGTT TGTTCTGTCT TCCCTGTAAG AAGCTCCCAG
20801 CATAAATATT CTAAATTTTA CACTACTAAT CTATTAACCA ACCTTTGGAC
20851 CATGTTCACT TTAGGTTGAG CATAGTGTGA TGAGATGCAA ATTAAATTAC
20901 AATCCTATAG GTGTGTGTTA TAAATTTTAA AGTGTATAAA TTAAATAACA
20951 CATTCTAAGT ATCCAACAAA GGTCAAAAAA ATGATATAAA GTCACCAAAC  (SEQ ID NO:3)
```

FEATURES:
Start:     197
Exon:      197-911
Intron:    912-6498
Exon:      6499-6647
Intron:    6648-15412
Exon:      15413-15544
Intron:    15545-16929
Exon:      16930-16940
Intron:    16941-17632
Exon:      17633-17712
Intron:    17713-18101
Exon:      18102-18321
Intron:    18322-18774
Exon:      18775-19051
Stop:      19052

CHROMOSOME MAP POSITION:
Chromosome 4

ALLELIC VARIANTS (SNPs):
DNA

| Position | Major | Minor | Domain |
|---|---|---|---|
| 1735 | A | G | Intron |
| 1922 | A | G | Intron |
| 2361 | C | T | Intron |
| 7371 | G | C | Intron |
| 9558 | G | A | Intron |
| 10579 | T | G A | Intron |
| 10625 | C | T | Intron |
| 11147 | A | G | Intron |
| 15131 | C | T G | Intron |
| 15221 | A | G T | Intron |
| 15778 | T | C | Intron |
| 15895 | – | A | Intron |
| 19786 | – | T | Beyond ORF(3') |
| 20157 | G | A | Beyond ORF(3') |
| 20246 | T | C | Beyond ORF(3') |
| 20681 | C | A | Beyond ORF(3') |
| 20819 | T | C | Beyond ORF(3') |

FIGURE 3H

Context:

| DNA Position | |
|---|---|
| 1735 | TACTTTACTGATATACACCTATTTGACTTATTTTTATTTCTTTGCTTTACTGATAAAAAG<br>TTGTTTTGCTTTGCAATTTTCATATAGTTGTGATCAGAGCTGGTCAATGCAAGACATGTT<br>TTTATCCAAATATGTTTGAGAATTATGTAGAAACATGAAAAAAGGTACAATTATATCCGA<br>CACTAAAATATTGTTTAATGTATTCCAACGAATTCTTATGCATAGACTGTTTCACAGAAC<br>TAATATTCAGAGGATCCCAGTTCAAATGTCCTTAGCCTTAGACATGATTTGAATTTACAT<br>[A,G]<br>TATTGATTTGCTTTAAATAATTTTCCATTCAGTAAGCTGTGCCTAGCTGCAGATAGCCTA<br>CCAGGCTTTATGGATCTAGGTAAACAATACAAATCTCTTGGCCTCAAGTCTACATTCAGA<br>TATTAATTTAAAGGGGTACAGCTATATAGAGGTCACTGGCAAATTTTGGTAAAATAGGAT<br>TATAGTAAAAGCCCCCTGACAAGATTGAAATTTAAAATAAAACAAAAGTGTTATCAAAGG<br>GGTGAAAGAGCATTTTCCAATAAACAAAAGTGGGTTCTGGCCATGCATTCAGAAATTCCC |
| 1922 | ATATTGTTTAATGTATTCCAACGAATTCTTATGCATAGACTGTTTCACAGAACTAATATT<br>CAGAGGATCCCAGTTCAAATGTCCTTAGCCTTAGACATGATTTGAATTTACATATATTGA<br>TTTGCTTTAAATAATTTTCCATTCAGTAAGCTGTGCCTAGCTGCAGATAGCCTACCAGGC<br>TTTATGGATCTAGGTAAACAATACAAATCTCTTGGCCTCAAGTCTACATTCAGATATTAA<br>TTTAAAGGGGTACAGCTATATAGAGGTCACTGGCAAATTTTGGTAAAATAGGATTATAGT<br>[A,G]<br>AAAGCCCCCTGACAAGATTGAAATTTAAAATAAAACAAAAGTGTTATCAAAGGGGTGAAA<br>GAGCATTTTCCAATAAACAAAAGTGGGTTCTGGCCATGCATTCAGAAATTCCCCAACAAT<br>TCTTTAAAAATCATGGAGCAGCTTGATATATAAGAAATTCATTTAATAACTATATTTATT<br>ATGTAGCTCCAACTTACTAAATTATTGATTATTATATATTTTATAGAATTATCTATTGTG<br>AGTCTAAATCAAGAGTATATATTCAAACAACTATAGGAAAAGGGATATCAGTCAATTTCA |
| 2361 | CAGCTTGATATATAAGAAATTCATTTAATAACTATATTTATTATGTAGCTCCAACTTACT<br>AAATTATTGATTATTATATATTTTATAGAATTATCTATTGTGAGTCTAAATCAAGAGTAT<br>ATATTCAAACAACTATAGGAAAAGGGATATCAGTCAATTTCAATTCAAGGATTTATTTCC<br>ATAAGTGCTTACGCACAGGTGTATTTCATTTTATTATACATTGCTTTATTGTCCTTCACA<br>AAAATTGCAATTTACAAATTAAAGGTTTTTGAAAACCTTGAATCAAGCTAATCAATTTGG<br>[C,T]<br>GTAATATTTCCAACAACAAGTGTGTACTTTTGACTCTATCACATATTGGCATTTATCATG<br>CTTTTTCAAATTTTTCATTGTTATATCTGTTACGGTGATCTGGGATCAGTGTTCCTTGAT<br>GGTTACACGTTTATTAGCTTGGGGGCACCTTGATGTGTTACAATATAAGACAGCAAACTT<br>AATTATAAATGTTGTGCATGTACTAACTGCTCCGCTGATTCGTTTCCCCATCCCACTTCT<br>TCTTAGGCCTCCCTATTCCCTGAGACACAGTAATATAACATACAATGACTTCTAAATGTT |
| 7371 | AAATAAGTGATGAAGGAAGACAAAGAATAAAAGAAAATTTCAATAAATGGAAAGTTTAAG<br>TGTTTAATGATAGTGATGACTTTTACTCAAATAAGTGCTTAGAAGTCATCTTGTTTGTGA<br>TTTATATGATGAATTCTGTGTTGTGACTATCCACTTTGAGCTCGTGAGAATGTTAGGTGA<br>GGTTTAATAAAAGCCATTTGAGAAAAACAAGGTTTCAACCTCTGTGGACAGAAATCTAAA<br>TATCGATAGTTATCAGGACAAAGTAGAGCTCATAGAAATAATTTTGCAGCCTGCAGGTTT<br>[G,C]<br>TTTTGGAGTGAAAATAAAATTGTATACTATATTCCTAAATCATCAGAGGAAAAAATTTAT<br>AGTTCAAGGAATGTTGAAAGAAACAATATTGAGAAGTAAAAGTGAGTAATAGTTGTTATA<br>GTTTTTTAATAGTTTTGTAAGTATGTCTTGAGTTCACTGTCCCAAAAGTGGCTATTAGCT<br>CTAGCCTTGACCTGACAAGGTTCTAGGATATTTAGTCATGGATGTTCATAATCTACCTCT<br>TACGGGATACTTTTTATTCTGATGAACAGCCTAATGCCTAAGTGTGCAATCTATACCAAG |
| 9558 | TCCACATATAAGGGATACCATGCTATCTCTGCCTGGATTATTTCAGTTAACATTATGCCC<br>TGGAGGTTCATTCATGTTTCTACAAATGACAGGATTTCATTCTTTTTTTTCCAATATATA<br>TTTAATGAAATGGATATATATAAACATTGGAAAATGTATATATATATATATATCTCCAGT<br>GGAATGCTATTGAGCTATAAAAAAGTTAATATATAATAGAAATAAAGCTTATATATATCT<br>AATGGAATGGATATATATATATAATGGAATAGAAATATATATCTATACATATAAACACAC<br>[G,A] |

FIGURE 3I

```
        CAATATACATATCCATTTCATTGCATATATATATATATAGAGAGAGAGAGAGAGAGATAT
        TTTCAAATGTGTGTATATATATCCAATGGAATGGACATATATATATGTATATTTTTTCCA
        TATTTTCTTTATGTATTTCTTCATTAATGGATGTTTAGGTTGATTCATCCCTTGGGTATA
        TGAATAATGTTGATGTAAACATAGAAGGACAGATATCTCTATGACTTCTTAGTTTATTTA
        AATATACACCCAGTAATGGAAATGCTGTATAATATGGTAGTTCTATTTTCATTTTTTGAG

10579   CAATGCTTTGATATAACCCATTTATCTACTTTTCCTTTTGTTGGCTGTGCTTCTGAAGTC
        CTATCCAAAAAAATCCTTGCCTAGACCAATGTCACAAATCATTCCTCCTACAGTTTCTTC
        TAGTAGTTGTATAATGTTTGGCCTTATATTTAACTTTGTAATTCATTTTTACTTACTTTG
        TATATGGTGAGGGATAGAGGTCTAGTTTCATTTTCTGCATGTGGATATGCAGTTTTCCTA
        GCACCATTTAGTGAAGAGGTTGCCTTTTTTCTATTATGTGTTCTTGGCACCTTTGTCAAA
        [T,G,A]
        GTCAGTTAGCTGCTATATTCCTCCATTTGTGTTGTTATAGAGGAACACATGAGACTAGCA
        AATTTATATATCAAATAGAATTATTTGAATGATAGTTCTGCATACTGTACAAGAAGCACA
        GCACTGACTTCTGCTTGGCCTCTGGTAAGGTTCTCAAGATGCTTCCACTTGTGGTAGAAG
        GCAAACATGAGCTGGTATATGCAAAGGTCTCATGACAAGAGAGGAAACCATAAAGAGGGG
        ATGTGAGGGAGTGCCAGGTTTTGTAAAACAACTAGCTCTTCTGGGAACTAATAGAGTAAA

10625   GTGCTTCTGAAGTCCTATCCAAAAAAATCCTTGCCTAGACCAATGTCACAAATCATTCCT
        CCTACAGTTTCTTCTAGTAGTTGTATAATGTTTGGCCTTATATTTAACTTTGTAATTCAT
        TTTTACTTACTTTGTATATGGTGAGGGATAGAGGTCTAGTTTCATTTTCTGCATGTGGAT
        ATGCAGTTTTCCTAGCACCATTTAGTGAAGAGGTTGCCTTTTTTCTATTATGTGTTCTTG
        GCACCTTTGTCAAAAGTCAGTTAGCTGCTATATTCCTCCATTTGTGTTGTTATAGAGGAA
        [C,T]
        ACATGAGACTAGCAAATTTATATATCAAATAGAATTATTTGAATGATAGTTCTGCATACT
        GTACAAGAAGCACAGCACTGACTTCTGCTTGGCCTCTGGTAAGGTTCTCAAGATGCTTCC
        ACTTGTGGTAGAAGGCAAACATGAGCTGGTATATGCAAAGGTCTCATGACAAGAGAGGAA
        ACCATAAAGAGGGGATGTGAGGGAGTGCCAGGTTTTGTAAAACAACTAGCTCTTCTGGGA
        ACTAATAGAGTAAAAAATTCGCCTCCCAGGCAGGGGATTAATCTATTCATGAGGGATCTGC

11147   ACAACTAGCTCTTCTGGGAACTAATAGAGTAAAAATTCGCCTCCCAGGCAGGGGATTAAT
        CTATTCATGAGGGATCTGCTTCCATGACAAAGGCACATTCTGTTAGATTCTACCCCCAAT
        ATTGGGGATCAAATTTTAACATGAAGTGTGGAGGGCTCAAATATCCATACTATGGCAGCA
        GTAAATGCATAAATTTATTTTGTGGATCTCTATTCTATATAGTATTGGTGTATGTATCTG
        TTTTCATGCCACTGCCATACTGTTTTGGTGATGATATCTATGCTATATATGTGTGTGTGT
        [A,G]
        TATATATATTATATATATGTATATATGTGTATATTATATATATGTATATATGTGTATATT
        ATATATATATAATACTTTAAGTTTTATATATATATAAAATACTTTAAGTTCAAGGGTACA
        TGTGCAGGATGTGCAGGTCAGTTACATAGGTATACATGTGCCATTTTGGTTTGCTGCATG
        CATCAACTCATCATTACATTAGGTATTTCTCCTAATGCTATCCCTCCACCAGCCACCCAA
        CCCCCAACAGGCCAGGTGTGTGATGTTCCCCGCCCTGTGTCCATGTGTTCTCATTGTTCA

15131   CAGGGAAGTTTTCTGTGACTGATGCTATTTTGGTTTGGAGAATGGGGTGATGTGGCACAA
        TGATCTTTCTTCTTTCTGGTCATGGATTTTTAATTTCCATGAACCCATAAGATTTTTCA
        CTTTTCTTCTGAGCTCTGGTGCTTTCAGAGTGGTATTTTTATATTCGAATAGTTGCTAGT
        TGTACTTTTAAAAGCGATTGATGCTGGAGGTCTTCTATTCCACCATCTCGCTGATGTCAG
        TCCTCAAATAATAATTTTATATTTTAGCAAATTATTTTGGTTTTAGGATTTTGTGTCTAC
        [C,T,G]
        TGACACAGACATGAAAAGAGATGTACTCATTACTGAAACTTTTTGCATACTGTTTTGGTT
        GTGCGCCTTTTCTAGTATGAATGATTACATATTTAAGCCACATGTTTTATACATAGACTG
        TCCTTTAAAGAGACTAGATAGTTCTGTGTGTCAGCATATAGGGACAGAATATAACTACAC
        ATTAATAATTTCTCAAGTATTTATTTTAGAAGTGTAAGTAACCTTTATTTTAATTTTTGT
        TATATTATGCCTCTGTAATGCAGATAAATTTTTATCTTCAGGAAATGGAAAATTTTGTCC

15221   TTAATTTCCATGAACCCATAAGATTTTTCACTTTTCTTCTGAGCTCTGGTGCTTTCAGAG
        TGGTATTTTTATATTCGAATAGTTGCTAGTTGTACTTTTAAAAGCGATTGATGCTGGAGG
        TCTTCTATTCCACCATCTCGCTGATGTCAGTCCTCAAATAATAATTTTATATTTTAGCAA
        ATTATTTTGGTTTTAGGATTTTGTGTCTACGTGACACAGACATGAAAAGAGATGTACTCA
```

FIGURE 3J

```
            TTACTGAAACTTTTTGCATACTGTTTTGGTTGTGCGCCTTTTCTAGTATGAATGATTACA
            [A,G,T]
            ATTTAAGCCACACATGTTTTATACATAGACTGTCCTTTAAAGAGACTAGATAGTTCTGTGTG
            TCAGCATATAGGGACAGAATATAACTACACATTAATAATTTCTCAAGTATTTATTTTAGA
            AGTGTAAGTAACCTTTATTTTAATTTTTGTTATATTATGCCTCTGTAATGCAGATAAATT
            TTTATCTTCAGGAAATGGAAATTTTGTCCAGAGTTCAGGGGAAGATGGTATTGTGGTGT
            TTTCTCTGGGGTCACTGTTTCAAAATGTTACAGAAGAAAAGGCTAATATCATTGCTTCAG

15778       GTTTCAAAATGTTACAGAAGAAAAGGCTAATATCATTGCTTCAGCCCTTGCCCAGATCCC
            ACAGAAGGTCAGTAAAACCTCCAATCCTGATAAGCAGCTATTCACATAATGAAACAGTAT
            GGTTTTATTTGGGTCTTGAATCTCATTTTCCACTTAGCATAACAGGTACCAAAATTTGCA
            AAACATTATAGTAGTGTACATGGGCATAACTGATCATTTGCCTACTGAGTCTTGCTGTTA
            CTGGAAACAACTTTCTTGATTGTCATTTGTTTATAATAAAATAGATATAATAAATAAAGC
            [T,C]
            CTACCTTATATTTTAGGATTTGAAATCTAAAAGCGTGTGCCAATGATTCCAAAAAAAAAT
            TCTGACATCTATTATTTCAAAGGACCAGAAAAAGGAAAACTGATATAAAAAAAAAAAGAA
            GAATCAATCTCAAGAATATCTTCTCATATTTGTGTGTATAAAAACTGTATTCAGGGTAGT
            TTTGCTTAGAAATAAAAGCTCAGATTAATGTAGTCTTTCTAAATAATTAGAAGTTTCAAA
            AGTAAAATGTCAATTACAATTATAGTATAGTAACAATTATTTAAGTAATGTAATTATTTA

15895       TATGGTTTTATTTGGGTCTTGAATCTCATTTTCCACTTAGCATAACAGGTACCAAAATTT
            GCAAAACATTATAGTAGTGTACATGGGCATAACTGATCATTTGCCTACTGAGTCTTGCTG
            TTACTGGAAACAACTTTCTTGATTGTCATTTGTTTATAATAAAATAGATATAATAAATAA
            AGCTCTACCTTATATTTTAGGATTTGAAATCTAAAAGCGTGTGCCAATGATTCCAAAAAA
            AAATTCTGACATCTATTATTTCAAAGGACCAGAAAAAGGAAAACTGATATAAAAAAAAAA
            [-,A]
            GAAGAATCAATCTCAAGAATATCTTCTCATATTTGTGTGTATAAAAACTGTATTCAGGGT
            AGTTTTGCTTAGAAATAAAAGCTCAGATTAATGTAGTCTTTCTAAATAATTAGAAGTTTC
            AAAAGTAAAATGTCAATTACAATTATAGTATAGTAACAATTATTTAAGTAATGTAATTAT
            TTATGATACTCCACTAATTTTAACTTTATTATTACTGTAATTCTAGAATTTCACACTTTA
            GATAGTGCTATATATAAACTATCCAAAAGATATTTCATTTTATATTTAGCTAAAATACTT

19786       GAAACATAATGATGTTTCTTTTTCAATTTAAATAAGCCCTTCTACATAGCCAGCATCAGT
            GATCTCAGAAAATAAATTGCTAATAATGATGACATGGCATTATGCTTAGAAAAGTTTGCT
            GTATTTCCATAGACCTCATCTAGATGTCATGGCCTACATTTCTGCCATCACTCAACCAAT
            ACTTTTTTCTGTTTTCTTGATGATAAAAAGACCTTTCTCATGATTGCCATCAAATAACAA
            AAGAAACTATTTTTTTTCTCACATAGAGAACATGTCAGTAAGATATTCAAGGTGAACAGA
            [-,T]
            ATTTTTGGGATTAGTAACTATTTGAAATATGTGGTGATAATTACTGAGTTTATAAAATTT
            ATTTGATAGTACACTTAAAGAAGATTTATATGTTTATTCTTTAAAAATGATGAATACTCA
            TAATTCTTATCTCTATAATCAAAAGTATAATTTACTGTAGAAAAATAAAGAGATGCTTGT
            TCTGAAAGTAAGATCAGTGAACTGCTTTTCAGTCTCAATCTTTGAGAATTGTAAATTCAT
            CAAATAATTGCTTACATAGTAAAAATTTAAGGTATTAGAAAACCTGCATAACAAATAGTA

20157       ACACTTAAAGAAGATTTATATGTTTATTCTTTAAAAATGATGAATACTCATAATTCTTAT
            CTCTATAATCAAAAGTATAATTTACTGTAGAAAAATAAAGAGATGCTTGTTCTGAAAGTA
            AGATCAGTGAACTGCTTTTCAGTCTCAATCTTTGAGAATTGTAAATTCATCAAATAATTG
            CTTACATAGTAAAAATTTAAGGTATTAGAAAACCTGCATAACAAATAGTATTATATATTA
            AATATTTTGATATGTAAAGCTCTACACAAAGCTAAATATAGTGTAATAATGTTTACACTA
            [G,A]
            TAAGCAAATATGTTAATCTTCTCATTTTTTACTGTCATATAATCTTAGTGATATGCCTA
            TTAATAGTTTTAAATAAATAAATTGGCTTATCTGGCTTTTTGAAAATTTTGAAATTCTTA
            CAGATGTTGATTAGGTATATCTACAAATTAATTTCATTTTAAAATGATGATATAAAAAT
            AAATATAAGTATTTTTCTTGTGTATGTATACAATAAATATAAATAAAATTGTTTACTGTT
            TTGAAAGTTTCTTAAGTTTTTACACTGATATGTTTTTTGACTTTTACAATATTATTATAA

20246       GAAAAATAAAGAGATGCTTGTTCTGAAAGTAAGATCAGTGAACTGCTTTTCAGTCTCAAT
            CTTTGAGAATTGTAAATTCATCAAATAATTGCTTACATAGTAAAAATTTAAGGTATTAGA
```

FIGURE 3K

```
        AAACCTGCATAACAAATAGTATTATATATTAAATATTTTGATATGTAAAGCTCTACACAA
        AGCTAAATATAGTGTAATAATGTTTACACTAGTAAGCAAATATGTTAATCTTCTCATTTT
        TTTACTGTCATATAATCTTAGTGATATGCCTATTAATAGTTTTAAATAAATAAATTGGCT
        [T,C]
        ATCTGGCTTTTTGAAAATTTTGAAATTCTTACAGATGTTGATTAGGTATATCTACAAATT
        AATTTCAATTTTAAAATGATGATATAAAAATAAATATAAGTATTTTTCTTGTGTATGTAT
        ACAATAAATATAAATAAAATTGTTTACTGTTTTGAAAGTTTCTTAAGTTTTTACACTGAT
        ATGTTTTTTGACTTTTACAATATTATTATAATCTAGGAAAAGCTGATTATATCTGTTTTA
        AGCCTCATCTTTTCTCTGTAATTAAACACAGTAATTTATTAACATGCTGTGACAGGTGGG

20681   TAAAATTGTTTACTGTTTTGAAAGTTTCTTAAGTTTTTACACTGATATGTTTTTTGACTT
        TTACAATATTATTATAATCTAGGAAAAGCTGATTATATCTGTTTTAAGCCTCATCTTTTC
        TCTGTAATTAAACACAGTAATTTATTAACATGCTGTGACAGGTGGGAAGCCATTTCTGGA
        GTTGAGCCTGCTGACACTCTGGAGCTTTTTAGGTTGGACGTTCATTGTATGTGGGACTCT
        CTGCCTCTCGATAGCTGTTGCTCATAAGACTCTCCTTCATCAATCTGGCATTGAATTTTG
        [C,A]
        GATCAGTTGCAATCAGAATCCAATTGGCCTTGCCGTTTTAGTATGTTCTATCTTAACCAG
        CAATTTCTAACCAGGAGCCTGCCCAGGTTTGTTCTGTCTTCCCTGTAAGAAGCTCCCAGC
        ATAAATATTCTAAATTTTACACTACTAATCTATTAACCAACCTTTGGACCATGTTCACTT
        TAGGTTGAGCATAGTGTGATGAGATGCAAATTAAATTACAATCCTATAGGTGTGTGTTAT
        AAATTTTAAAGTGTATAAATTAAATAACACATTCTAAGTATCCAACAAAGGTCAAAAAAA

20819   AATTTATTAACATGCTGTGACAGGTGGGAAGCCATTTCTGGAGTTGAGCCTGCTGACACT
        CTGGAGCTTTTTAGGTTGGACGTTCATTGTATGTGGGACTCTCTGCCTCTCGATAGCTGT
        TGCTCATAAGACTCTCCTTCATCAATCTGGCATTGAATTTTGCGATCAGTTGCAATCAGA
        ATCCAATTGGCCTTGCCGTTTTAGTATGTTCTATCTTAACCAGCAATTTCTAACCAGGAG
        CCTGCCCAGGTTTGTTCTGTCTTCCCTGTAAGAAGCTCCCAGCATAAATATTCTAAATTT
        [T,C]
        ACACTACTAATCTATTAACCAACCTTTGGACCATGTTCACTTTAGGTTGAGCATAGTGTG
        ATGAGATGCAAATTAAATTACAATCCTATAGGTGTGTGTTATAAATTTTAAAGTGTATAA
        ATTAAATAACACATTCTAAGTATCCAACAAAGGTCAAAAAAATGATATAAAGTCACCAAA
        C
```

FIGURE 3L

ISOLATED NUCLEIC ACID MOLECULES ENCODING HUMAN DRUG METABOLIZING PROTEINS

RELATED APPLICATIONS

The present application claims priority to provisional applications U.S. Ser. No. 60/228,893 filed Aug. 30, 2000.

FIELD OF THE INVENTION

The present invention is in the field of drug-metabolizing proteins that are related to the UDP-glucuronosyltransferase drug-metabolizing enzyme subfamily, recombinant DNA molecules and protein production. The present invention specifically provides novel drug-metabolizing peptides and proteins and nucleic acid molecules encoding such protein molecules, for use in the development of human therapeutics and human therapeutic development.

BACKGROUND OF THE INVENTION

Drug-Metabolizing Proteins

Induction of drug-metabolizing enzymes ("DMEs") is a common biological response to xenobiotics, the mechanisms and consequences of which are important in academic, industrial, and regulatory areas of pharmacology and toxicology.

For most drugs, drug-metabolizing enzymes determine how long and how much of a drug remains in the body. Thus, developers of drugs recognize the importance of characterizing a drug candidate's interaction with these enzymes. For example, polymorphisms of the drug-metabolizing enzyme CYP2D6, a member of the cytochrome p450 ("CYP") superfamily, yield phenotypes of slow or ultra-rapid metabolizers of a wide spectrum of drugs including antidepressants, antipsychotics, beta-blockers, and antiarrhythmics. Such abnormal rates of drug metabolism can lead to drug ineffectiveness or to systemic accumulation and toxicity.

For pharmaceutical scientists developing a candidate drug, it is important know as early as possible in the design phase which enzymes metabolize the drug candidate and the speed with which they do it. Historically, the enzymes on a drug's metabolic pathway were determined through metabolism studies in animals, but this approach has now been largely supplanted by the use of human tissues or cloned drug-metabolizing enzymes to provide insights into the specific role of individual forms of these enzymes. Using these tools, the qualitative and quantitative fate of a drug candidate can be predicted prior to its first administration to humans. As a consequence, the selection and optimization of desirable characteristics of metabolism are possible early in the development process, thus avoiding unanticipated toxicity problems and associated costs subsequent to the drug's clinical investigation. Moreover, the effect of one drug on another's disposition can be inferred.

Known drug-metabolizing enzymes include the cytochrome p450 ("CYP") superfamily, N-acetyl transferases ("NAT"), UDP-glucuronosyl transferases ("UGT"), methyl transferases, alcohol dehydrogenase ("ADH"), aldehyde dehydrogenase ("ALDH"), dihydropyrimidine dehydrogenase ("DPD"), NADPH:quinone oxidoreductase ("NQO" or "DT diaphorase"), catechol 0-methyltransferase ("COMT"), glutathione S-transferase ("GST"), histamine methyltransferase ("HMT"), sulfotransferases ("ST"), thiopurine methyltransferase ("TPMT"), and epoxide hydroxylase. Drug-metabolizing enzymes are generally classified into two phases according to their metabolic function. Phase I enzymes catalyze modification of functional groups, and phase II enzymes catalyze conjugation with endogenous substituents. These classifications should not be construed as exclusive nor exhaustive, as other mechanisms of drug metabolism have been discovered. For example, the use of active transport mechanisms been characterized as part of the process of detoxification.

Phase I reactions include catabolic processes such as deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum.

Phase II enzymes detoxify toxic substances by catalyzing their conjugation with water-soluble substances, thus increasing toxins' solubility in water and increasing their rate of excretion. Additionally, conjugation reduces the toxins' biological reactivity. Examples of phase II enzymes include glutathione S-transferases and UDP-glucuronosyl transferases, which catalyze conjugation to glutathione and glucuronic acid, respectively. Transferases perform conjugation reactions mainly in the kidneys and liver.

The liver is the primary site of elimination of most drugs, including psychoactive drugs, and contains a plurality of both phase I and phase II enzymes that oxidize or conjugate drugs, respectively.

Physicians currently prescribe drugs and their dosages based on a population average and fail to take genetic variability into account. The variability between individuals in drug metabolism is usually due to both genetic and environmental factors, in particular, how the drug-metabolizing enzymes are controlled. With certain enzymes, the genetic component predominates and variability is associated with variants of the normal, wild-type enzyme.

Most drug-metabolizing enzymes exhibit clinically relevant genetic polymorphisms. Essentially all of the major human enzymes responsible for modification of functional groups or conjugation with endogenous subsituents exhibit common polymorphisms at the genomic level. For example, polymorphisms expressing a non-functioning variant enzyme results in a sub-group of patients in the population who are more prone to the concentration-dependent effects of a drug. This sub-group of patients may show toxic side effects to a dose of drug that is otherwise without side effects in the general population. Recent development in genotyping allows identification of affected individuals. As a result, their atypical metabolism and likely response to a drug metabolized by the affected enzyme can be understood and predicted, thus permitting the physician to adjust the dose of drug they receive to achieve improved therapy.

A similar approach is also becoming important in identifying risk factors associated with the development of various cancers. This is because the enzymes involved in drug metabolism are also responsible for the activation and detoxification of chemical carcinogens. Specifically, the development of neoplasia is regulated by a balance between phase I enzymes, which activate carcinogens, and phase II enzymes, which detoxify them. Accordingly, an individual's susceptibility to cancer often involves the balance between these two processes, which is, in part, genetically determined and can be screened by suitable genotyping tests.

Higher induction of phase I enzymes compared to phase II enzymes results in the generation of large amounts of electrophiles and reactive oxygen species and may cause DNA and membrane damage and other adverse effects leading to neoplasia. Conversely, higher levels of phase II enzyme expression can protect cells from various chemical compounds.

Abnormal activity of drug-metabolizing enzymes has been implicated in a range of human diseases, including cancer, Parkinson's disease, myetonic dystrophy, and developmental defects.

Cytochrome p450

An example of a phase I drug-metabolizing enzyme is the cytochrome p450 ("CYP") superfamily, the members of which comprise the major drug-metabolizing enzymes expressed in the liver. The CYP superfamily comprises heme proteins which catalyze the oxidation and dehydrogenation of a number of endogenous and exogenous lipophilic compounds. The CYP superfamily has immense diversity in its functions, with hundreds of isoforms in many species catalyzing many types of chemical reactions. The CYP superfamily comprises at least 30 related enzymes, which are divided into different families according to their amino acid homology. Examples of CYP families include CYP families 1, 2, 3 and 4, which comprise endoplasmic reticulum proteins responsible for the metabolism of drugs and other xenobiotics. Approximately 10–15 individual gene products within these four families metabolize thousands of structurally diverse compounds. It is estimated that collectively the enzymes in the CYP superfamily participate in the metabolism of greater than 80% of all available drugs used in humans. For example, the CYP 1A subfamily comprises CYP 1A2, which metabolizes several widely used drugs, including acetaminophen, amitriptyline, caffeine, clozapine, haloperidol, imipramine, olanzapine, ondansetron, phenacetin, propafenone, propranolol, tacrine, theophylline, verapamil. In addition, CYP enzymes play additional roles in the metabolism of some endogenous substrates including prostaglandins and steroids.

Some CYP enzymes exist in a polymorphic form, meaning that a small percentage of the population possesses mutant genes that alter the activity of the enzyme, usually by diminishing or abolishing activity. For example, a genetic polymorphism has been well characterized with the CYP 2C19 and CYP 2D6 genes. Substrates of CYP 2C19 include clomipramine, diazepam, imipramine, mephenytoin, moclobemide, omeprazole, phenytoin, propranolol, and tolbutamide. Substrates of CYP 2D6 include alprenolol, amitriptyline, chlorpheniramine, clomipramine, codeine, desipramine, dextromethorphan, encainide, fluoxetine, haloperidol, imipramine, indoramin, metoprolol, nortriptyline, ondansetron, oxycodone, paroxetine, propranolol, and propafenone. Polymorphic variants of these genes metabolize these substrates at different rates, which can effect a patient's effective therapeutic dosage.

While the substrate specificity of CYPs must be very broad to accommodate the metabolism of all of these compounds, each individual CYP gene product has a narrower substrate specificity defined by its binding and catalytic sites. Drug metabolism can thereby be regulated by changes in the amount or activity of specific CYP gene products. Methods of CYP regulation include genetic differences in the expression of CYP gene products (i.e., genetic polymorphisms), inhibition of CYP metabolism by other xenobiotics that also bind to the CYP, and induction of certain CYPs by the drug itself or other xenobiotics. Inhibition and induction of CYPs is one of the most common mechanisms of adverse drug interactions. For example, the CYP3A subfamily is involved in clinically significant drug interactions involving nonsedating antihistamines and cisapride that may result in cardiac dysrhythmias. In another example, CYP3A4 and CYP1A2 enzymes are involved in drug interactions involving theophylline. In yet another example, CYP2D6 is responsible for the metabolism of many psychotherapeutic agents. Additionallly, CYP enzymes metabolize the protease inhibitors used to treat patients infected with the human immunodeficiency virus. By understanding the unique functions and characteristics of these enzymes, physicians may better anticipate and manage drug interactions and may predict or explain an individual's response to a particular therapeutic regimen.

Examples of reactions catalyzed by the CYP superfamily include peroxidative reactions utilizing peroxides as oxygen donors in hydroxylation reactions, as substrates for reductive beta-scission, and as peroxyhemiacetal intermediates in the cleavage of aldehydes to formate and alkenes. Lipid hydroperoxides undergo reductive beta-cleavage to give hydrocarbons and aldehydic acids. One of these products, trans-4-hydroxynonenal, inactivates CYP, particularly alcohol-inducible 2E1, in what may be a negative regulatory process. Although a CYP iron-oxene species is believed to be the oxygen donor in most hydroxylation reactions, an iron-peroxy species is apparently involved in the deformylation of many aldehydes with desaturation of the remaining structure, as in aromatization reactions.

Examples of drugs with oxidative metabolism associated with CYP enzymes include acetaminophen, alfentanil, alprazolam, alprenolol, amiodarone, amitriptyline, astemizole, buspirone caffeine, carbamazepine, chlorpheniramine, cisapride, clomipramine, clomipramine, clozapine, codeine, colchicine, cortisol, cyclophosphamide, cyclosporine, dapsone, desipramine, dextromethorphan, diazepam, diclofenac, diltiazem, encainide, erythromycin, estradiol, felodipine, fluoxetine, fluvastatin, haloperidol, ibuprofen, imipramine, indinavir, indomethacin, indoramin, irbesartan, lidocaine, losartan, macrolide antibiotics, mephenytoin, methadone, metoprolol, mexilitene, midazolam, moclobemide, naproxen, nefazodone, nicardipine, nifedipine, nitrendipine, nortriptyline, olanzapine, omeprazole, ondansetron, oxycodone, paclitaxel, paroxetine, phenacetin, phenytoin, piroxicam, progesterone, propafenone, propranolol, quinidine, ritonavir, saquinavir, sertraline, sildenafil, S-warfarin, tacrine, tamoxifen, tenoxicam, terfenadine, testosterone, theophylline, timolol, tolbutamide, triazolam, verapamil, and vinblastine.

Abnormal activity of phase I enzymes has been implicated in a range of human diseases. For example, enhanced CYP2D6 activity has been related to malignancies of the bladder, liver, pharynx, stomach and lungs, whereas decreased CYP2D activity has been linked to an increased risk of Parkinson's disease. Other syndromes and developmental defects associated with deficiencies in the CYP superfamily include cerebrotendinous xanthomatosis, adrenal hyperplasia, gynecomastia, and myetonic dystrophy.

The CYP superfamily a major target for drug action and development. Accordingly, it is valuable to the field of pharmaceutical development to identify and characterize previously unknown members of the CYP superfamily.

UDP-Glucuronosyltransferases

Potential drug interactions involving phase II metabolism are increasingly being recognized. An important group of phase II enzymes involved in drug metabolism are the glucuronosyltransferases, especially the UDP-glucuronyltransferase ("UGT") superfamily. Members of the UGT superfamily catalyze the enzymatic addition of UDP glucuronic acid as a sugar donor to fat-soluble chemicals, a process which increases their solubility in water and increases their rate of excretion. In mammals, glucuronic acid is the main sugar that is used to prevent the accumulation of waste products of metabolism and fat-soluble chemicals from the environment to toxic levels in the body. Both inducers and inhibitors of glucuronosyltransferases are known and have the potential to affect the plasma concentration and actions of important drugs, including psychotropic drugs.

The UGT superfamily comprises several families of enzymes in several species defined with a nomenclature similar to that used to define members of the CYP superfamily. In animals, yeast, plants and bacteria there are at least 110 distinct known members of the UGT superfamily. As many as 33 families have been defined, with three families identified in humans. Different UGT families are defined as having <45% amino acid sequence homology; within subfamilies there is approximately 60% homology. The members of the UGT superfamily are part of a further superfamily of UDP glycosyltransferases found in animals, plants and bacteria.

The role of phase II enzymes, and of UGT enzymes in particular, is being increasingly recognized as important in psychopharmacology. UGT enzymes conjugate many important psychotropic drugs and are an important source of variability in drug response and drug interactions. For example, the benzodiazepines lorazepam, oxazepam, and temazepam undergo phase II reactions exclusively before being excreted into the urine.

Phase II enzymes metabolize and detoxify hazardous substances, such as carcinogens. The expression of genes encoding phase II enzymes is known to be up-regulated by hundreds of agents. For example, oltipraz is known to up-regulate phase II enzyme expression. Studies have demonstrated protection from the cancer-causing effects of carcinogens when selected phase II enzyme inducers are administered prior to the carcinogens. The potential use of phase II enzyme inducers in humans for prevention of cancers related to exposure to carcinogens has prompted studies aimed at understanding their molecular effects. Current biochemical and molecular biological research methodologies can be used to identify and characterize selective phase II enzyme inducers and their targets. Identification of genes responding to cancer chemopreventive agents will facilitate studies of their basic mechanism and provide insights about the relationship between gene regulation, enzyme polymorphism, and carcinogen detoxification.

Examples of drugs with conjugative metabolism associated with UGT enzymes include amitriptyline, buprenorphine, chlorpromazine, clozapine, codeine, cyproheptadine, dihydrocodeine, doxepin, imipramine, lamotrigine, lorazepam, morphine, nalorphine, naltrexone, temazepam, and valproate.

Abnormal activity of phase II enzymes has been implicated in a range of human diseases. For example, Gilbert syndrome is an autosomal dominant disorder caused by mutation in the UGT1 gene, and mutations in the UGT1A1 enzyme have been demonstrated to be responsible for Crigler-Najjar syndrome.

The UGT superfamily a major target for drug action and development. Accordingly, it is valuable to the field of pharmaceutical development to identify and characterize previously unknown members of the UGT superfamily.

For a further review of UDP-glucuronosyltransferases, see Jin et al., *Biochem Biophys Res Commun* 1993 Jul. 15; 194(1):496–503; Beaulieu et al., *Biochem Biophys Res Commun* 1998 Jul. 9; 248(1):44–50; Belanger et al., *DNA Cell Biol* 1997 Oct.; 16(10):1195–205; Jackson et al., *Biochem J* 1987 Mar. 1; 242(2):581–8; Taura et al., *Biochem Biophys Res Commun* 2000 Jul. 14; 273(3):1048–1052; Burchell et al., *DNA Cell Biol.* 10: 487–494, 1991; Krasnewich et al., *Somat. Cell Molec. Genet.* 13: 179–182, 1987; Monaghan et al., *Genomics* 23: 496–499, 1994; Monaghan et al., *Genomics* 13: 908–909, 1992; and Riedy et al., *Pharmacogenetics* 10: 251–260, 2000.

Drug-metabolizing enzymes, particularly members of the UDP-glucuronosyltransferase drug-metabolizing enzyme subfamily, are a major target for drug action and development. Accordingly, it is valuable to the field of pharmaceutical development to identify and characterize previously unknown members of this subfamily of drug-metabolizing proteins. The present invention advances the state of the art by providing a previously unidentified human drug-metabolizing proteins that have homology to members of the UDP-glucuronosyltransferase drug-metabolizing enzyme subfamily.

SUMMARY OF THE INVENTION

The present invention is based in part on the identification of amino acid sequences of human drug-metabolizing enzyme peptides and proteins that are related to the UDP-glucuronosyltransferase drug-metabolizing enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate drug-metabolizing enzyme activity in cells and tissues that express the drug-metabolizing enzyme. Experimental data as provided in FIG. 1 indicates expression in humans in the kidney (including kidney hypemephromas), liver (including fetal liver, HepG2 cell lines, and hepatocellular carcinomas), and pigmental retinal epithelium.

DESCRIPTION OF THE FIGURE SHEETS

FIG. 1 provides the nucleotide sequence of a cDNA molecule that encodes the drug-metabolizing enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the kidney (including kidney hypernephromas), liver (including fetal liver, HepG2 cell lines, and hepatocellular carcinomas), and pigmental retinal epithelium.

FIG. 2 provides the predicted amino acid sequence of the drug-metabolizing enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the drug-metabolizing enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 17 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a drug-metabolizing enzyme protein or part of a drug-metabolizing enzyme protein and are related to the UDP-glucuronosyltransferase drug-metabolizing enzyme subfamily. Utilizing these sequences, additional genomic sequences were assembled and transcript and/or cDNA sequences were isolated and characterized. Based on this analysis, the present invention provides amino acid sequences of human drug-metabolizing enzyme peptides and proteins that are related to the UDP-glucuronosyltransferase drug-metabolizing enzyme subfamily, nucleic acid sequences in the form of transcript sequences, cDNA sequences and/or genomic sequences that encode these drug-metabolizing enzyme peptides and proteins, nucleic acid variation (allelic information), tissue distribution of expression, and information about the closest art known protein/peptide/domain that has structural or sequence homology to the drug-metabolizing enzyme of the present invention.

In addition to being previously unknown, the peptides that are provided in the present invention are selected based on their ability to be used for the development of commercially important products and services. Specifically, the present peptides are selected based on homology and/or structural relatedness to known drug-metabolizing enzyme proteins of the UDP-glucuronosyltransferase drug-metabolizing enzyme subfamily and the expression pattern observed. Experimental data as provided in FIG. 1 indicates expression in humans in the kidney (including kidney hypernephromas), liver (including fetal liver, HepG2 cell lines, and hepatocellular carcinomas), and pigmental retinal epithelium. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known UDP-glucuronosyltransferase family or subfamily of drug-metabolizing enzyme proteins.

Specific Embodiments

Peptide Molecules

The present invention provides nucleic acid sequences that encode protein molecules that have been identified as being members of the drug-metabolizing enzyme family of proteins and are related to the UDP-glucuronosyltransferase drug-metabolizing enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the drug-metabolizing enzyme peptides of the present invention, drug-metabolizing enzyme peptides, or peptides/proteins of the present invention.

The present invention provides isolated peptide and protein molecules that consist of, consist essentially of, or comprise the amino acid sequences of the drug-metabolizing enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the drug-metabolizing enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated drug-metabolizing enzyme peptide can be purified from cells that naturally express it, purified from cells that have been altered to express it (recombinant), or synthesized using known protein synthesis methods. Experimental data as provided in FIG. 1 indicates expression in humans in the kidney (including kidney hypemephromas), liver (including fetal liver, HepG2 cell lines, and hepatocellular carcinomas), and pigmental retinal epithelium. For example, a nucleic acid molecule encoding the drug-metabolizing enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG.

2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the drug-metabolizing enzyme peptides of the present invention are the naturally occurring mature proteins. A brief description of how various types of these proteins can be made/isolated is provided below.

The drug-metabolizing enzyme peptides of the present invention can be attached to heterologous sequences to form chimeric or fusion proteins. Such chimeric and fusion proteins comprise a drug-metabolizing enzyme peptide operatively linked to a heterologous protein having an amino acid sequence not substantially homologous to the drug-metabolizing enzyme peptide. "Operatively linked" indicates that the drug-metabolizing enzyme peptide and the heterologous protein are fused in-frame. The heterologous protein can be fused to the N-terminus or C-terminus of the drug-metabolizing enzyme peptide.

In some uses, the fusion protein does not affect the activity of the drug-metabolizing enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant drug-metabolizing enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A drug-metabolizing enzyme peptide-encoding nucleic acid can be cloned into such an expression vector such that the fusion moiety is linked in-frame to the drug-metabolizing enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the drug-metabolizing enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, N.Y., 1993; *Computer Analysis of Sequence Data, Part 1*, Griffin, A. M., and Griffin, H. G., eds., Humana Press, N.J., 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg-.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the drug-metabolizing enzyme peptides of the present invention as well as being encoded by the same genetic locus as the drug-metabolizing enzyme peptide provided herein. The gene encoding the novel drug-metabolizing protein of the present invention is located on a genome component that has been mapped to human chromosome 4 (as indicated in FIG. 3), which is supported by multiple lines of evidence, such as STS and BAC map data.

Allelic variants of a drug-metabolizing enzyme peptide can readily be identified as being a human protein having a high degree (significant) of sequence homology/identity to at least a portion of the drug-metabolizing enzyme peptide as well as being encoded by the same genetic locus as the drug-metabolizing enzyme peptide provided herein. Genetic locus can readily be determined based on the genomic information provided in FIG. 3, such as the genomic sequence mapped to the reference human. The gene encoding the novel drug-metabolizing protein of the present invention is located on a genome component that has been mapped to human chromosome 4 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a drug-metabolizing enzyme peptide encoding nucleic acid molecule under stringent conditions as more fully described below.

FIG. 3 provides information on SNPs that have been found in the gene encoding the drug-metabolizing protein of the present invention. SNPs were identified at 17 different nucleotide positions. Some of these SNPs may affect control/regulatory elements.

Paralogs of a drug-metabolizing enzyme peptide can readily be identified as having some degree of significant sequence homology/identity to at least a portion of the drug-metabolizing enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a drug-metabolizing enzyme peptide encoding nucleic acid molecule under moderate to stringent conditions as more fully described below.

Orthologs of a drug-metabolizing enzyme peptide can readily be identified as having some degree of significant sequence homology/identity to at least a portion of the drug-metabolizing enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a drug-metabolizing enzyme peptide encoding nucleic acid molecule under moderate to stringent conditions, as more fully described below, depending on the degree of relatedness of the two organisms yielding the proteins.

Non-naturally occurring variants of the drug-metabolizing enzyme peptides of the present invention can readily be generated using recombinant techniques. Such variants include, but are not limited to deletions, additions and substitutions in the amino acid sequence of the drug-metabolizing enzyme peptide. For example, one class of substitutions are conserved amino acid substitution. Such substitutions are those that substitute a given amino acid in a drug-metabolizing enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–13 10 (1990).

Variant drug-metabolizing enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as drug-metabolizing enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J Mol. Biol.* 224:899–904 (1992); de Vos et al. *Science* 255:306–312 (1992)).

The present invention further provides fragments of the drug-metabolizing enzyme a peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a drug-metabolizing enzyme peptide. Such fragments can be chosen based on the ability to retain one or more of the biological activities of the drug-metabolizing enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the drug-metabolizing enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in drug-metabolizing enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y Acad. Sci.* 663:48–62 (1992)).

Accordingly, the drug-metabolizing enzyme peptides of the present invention also encompass derivatives or analogs in which a substituted amino acid residue is not one encoded by the genetic code, in which a substituent group is included, in which the mature drug-metabolizing enzyme peptide is fused with another compound, such as a compound to increase the half-life of the drug-metabolizing enzyme peptide (for example, polyethylene glycol), or in which the additional amino acids are fused to the mature drug-metabolizing enzyme peptide, such as a leader or secretory sequence or a sequence for purification of the mature drug-metabolizing enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a drug-metabolizing enzyme-effector protein interaction or drug-metabolizing enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, drug-metabolizing enzymes isolated from humans and their human/mammalian orthologs serve as targets for identifying agents for use in mammalian therapeutic applications, e.g. a human drug, particularly in modulating a biological or pathological response in a cell or tissue that expresses the drug-metabolizing enzyme. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver. A large percentage of pharmaceutical agents are being developed that modulate the activity of drug-metabolizing enzyme proteins, particularly members of the UDP-glucuronosyltransferase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the kidney (including kidney hypernephromas), liver (including fetal liver, HepG2 cell lines, and hepatocellular carcinomas), and pigmental retinal epithelium. Such uses can readily be determined using the information provided herein, that which is known in the art, and routine experimentation.

The drug-metabolizing enzyme polypeptides (including variants and fragments that may have been disclosed prior to the present invention) are useful for biological assays related to drug-metabolizing enzymes that are related to members of the UDP-glucuronosyltransferase subfamily. Such assays involve any of the known drug-metabolizing enzyme functions or activities or properties useful for diagnosis and treatment of drug-metabolizing enzyme-related conditions that are specific for the subfamily of drug-metabolizing enzymes that the one of the present invention belongs to, particularly in cells and tissues that express the drug-metabolizing enzyme. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver.

The drug-metabolizing enzyme polypeptides are also useful in drug screening assays, in cell-based or cell-free systems. Cell-based systems can be native, i.e., cells that normally express the drug-metabolizing enzyme, as a biopsy or expanded in cell culture. Experimental data as provided in FIG. 1 indicates expression in humans in the kidney (including kidney hypernephromas), liver (including fetal liver, HepG2 cell lines, and hepatocellular carcinomas), and pigmental retinal epithelium. In an alternate embodiment, cell-based assays involve recombinant host cells expressing the drug-metabolizing enzyme protein.

The polypeptides can be used to identify compounds that modulate drug-metabolizing enzyme activity of the protein in its natural state or an altered form that causes a specific disease or pathology associated with the drug-metabolizing enzyme. Both the drug-metabolizing enzymes of the present invention and appropriate variants and fragments can be used in high-throughput screens to assay candidate compounds for the ability to bind to the drug-metabolizing enzyme. These compounds can be further screened against a functional drug-metabolizing enzyme to determine the effect of the compound on the drug-metabolizing enzyme activity. Further, these compounds can be tested in animal or invertebrate systems to determine activity/effectiveness. Compounds can be identified that activate (agonist) or inactivate (antagonist) the drug-metabolizing enzyme to a desired degree.

Further, the drug-metabolizing enzyme polypeptides can be used to screen a compound for the ability to stimulate or inhibit interaction between the drug-metabolizing enzyme protein and a molecule that normally interacts with the drug-metabolizing enzyme protein. Such assays typically include the steps of combining the drug-metabolizing enzyme protein with a candidate compound under conditions that allow the drug-metabolizing enzyme protein, or fragment, to interact with the target molecule, and to detect the formation of a complex between the protein and the target or to detect the biochemical consequence of the interaction with the drug-metabolizing enzyme protein and the target.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant drug-metabolizing enzymes or appropriate fragments containing mutations that affect drug-metabolizing enzyme function and thus compete for substrate. Accordingly, a fragment that competes for substrate, for example with a higher affinity, or a fragment that binds substrate but does not allow release, is encompassed by the invention.

Any of the biological or biochemical functions mediated by the drug-metabolizing enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the drug-metabolizing enzyme can be assayed. Experimental data as provided in FIG. 1 indicates that the drug-metabolizing proteins of the present invention are expressed in humans in the kidney (including kidney hypemephromas), liver (including HepG2 cell lines and hepatocellular carcinomas), and pigmental retinal epithelium, as indicated by virtual northern blot analysis. In addition, PCR-based tissue screening panels indicate expression in human fetal liver.

Binding and/or activating compounds can also be screened by using chimeric drug-metabolizing enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native drug-metabolizing enzyme. Accordingly, a different set of signal transduction components is available as an end-point assay for activation. This allows for assays to be performed in other than the specific host cell from which the drug-metabolizing enzyme is derived.

The drug-metabolizing enzyme polypeptides are also useful in competition binding assays in methods designed to discover compounds that interact with the drug-metabolizing enzyme (e.g. binding partners and/or ligands). Thus, a compound is exposed to a drug-metabolizing enzyme polypeptide under conditions that allow the compound to bind or to otherwise interact with the polypeptide. Soluble drug-metabolizing enzyme polypeptide is also added to the mixture. If the test compound interacts with the soluble drug-metabolizing enzyme polypeptide, it decreases the amount of complex formed or activity from the drug-metabolizing enzyme target. This type of assay is particularly useful in cases in which compounds are sought that interact with specific regions of the drug-metabolizing enzyme. Thus, the soluble polypeptide that competes with the target drug-metabolizing enzyme region is designed to contain peptide sequences corresponding to the region of interest.

To perform cell free drug screening assays, it is sometimes desirable to immobilize either the drug-metabolizing enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of drug-metabolizing enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a drug-metabolizing enzyme-binding protein and a candidate compound are incubated in the drug-metabolizing enzyme protein-presenting wells and the amount of complex trapped in the well can be quantitated. Methods for detecting such complexes, in addition to those described above for the GST-immobilized complexes, include immunodetection of complexes using antibodies reactive with the drug-metabolizing enzyme protein target molecule, or which are reactive with drug-metabolizing enzyme protein and compete with the target molecule, as well as enzyme-linked assays which rely on detecting an enzymatic activity associated with the target molecule.

Agents that modulate one of the drug-metabolizing enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of drug-metabolizing enzyme protein activity identified according to these drug screening assays can be used to treat a subject with a disorder mediated by the drug-metabolizing enzyme pathway, by treating cells or tissues that express the drug-metabolizing enzyme. Experimental data as provided in FIG. 1 indicates expression in humans in the kidney (including kidney hypernephromas), liver (including fetal liver, HepG2 cell lines, and hepatocellular carcinomas), and pigmental retinal epithelium. These methods of treatment include the steps of administering a modulator of drug-metabolizing enzyme activity in a pharmaceutical composition to a subject in need of such treatment, the modulator being identified as described herein.

In yet another aspect of the invention, the drug-metabolizing enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J Biol. Chem.* 268:12046–12054; Bartel etal. (1993) *Biotechniques* 14:920–924; Iwabuchi et al. (1993) *Oncogene* 8:1693–1696; and Brent WO94/10300), to identify other proteins, which bind to or interact with the drug-metabolizing enzyme and are involved in drug-metabolizing enzyme activity. Such drug-metabolizing enzyme-binding proteins are likely to be drug-metabolizing enzyme inhibitors.

The two-hybrid system is based on the modular nature of most transcription factors, which consist of separable DNA-binding and activation domains. Briefly, the assay utilizes two different DNA constructs. In one construct, the gene that codes for a drug-metabolizing enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a drug-metabolizing enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the drug-metabolizing enzyme protein.

This invention further pertains to novel agents identified by the above-described screening assays. Accordingly, it is within the scope of this invention to further use an agent identified as described herein in an appropriate animal model. For example, an agent identified as described herein (e.g., a drug-metabolizing enzyme-modulating agent, an antisense drug-metabolizing enzyme nucleic acid molecule, a drug-metabolizing enzyme-specific antibody, or a drug-metabolizing enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The drug-metabolizing enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the kidney (including kidney hypernephromas), liver (including fetal liver, HepG2 cell lines, and hepatocellular carcinomas), and pigmental retinal epithelium. The method involves contacting a biological sample with a compound capable of interacting with the drug-metabolizing enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered drug-metabolizing enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the drug-metabolizing enzyme protein in which one or more of the drug-metabolizing enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and drug-metabolizing enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the kidney (including kidney hypernephromas), liver (including fetal liver, HepG2 cell lines, and hepatocellular carcinomas), and pigmental retinal epithelium. Accordingly, methods for treatment include the use of the drug-metabolizing enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the drug-metabolizing enzyme proteins. Antibodies can be prepared from any region of the peptide as described herein. However, preferred regions will include those involved in function/activity and/or drug-metabolizing enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the fall length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the kidney (including kidney hypemephromas), liver (including fetal liver, HepG2 cell lines, and hepatocellular carcinomas), and pigmental retinal epithelium. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the kidney (including kidney hypemephromas), liver (including fetal liver, HepG2 cell lines, and hepatocellular carcinomas), and pigmental retinal epithelium. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the kidney (including kidney hypemephromas), liver (including fetal liver, HepG2 cell lines, and hepatocellular carcinomas), and pigmental retinal epithelium. Thus, where a specific protein has been correlated with expression in a specific tissue, antibodies that are specific for this protein can be used to identify a tissue type.

The antibodies are also useful for inhibiting protein function, for example, blocking the binding of the drug-metabolizing enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a drug-metabolizing enzyme peptide or protein of the present invention (cDNA, transcript and genomic sequence). Such nucleic acid molecules will consist of, consist essentially of, or comprise a nucleotide sequence that encodes one of the drug-metabolizing enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated-"nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the drug-metabolizing enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the drug-metabolizing enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel drug-metabolizing protein of the present invention is located on a genome component that has been mapped to human chromosome 4 (as indicated in FIG. 3), which is supported by multiple lines of evidence, such as STS and BAC map data.

FIG. 3 provides information on SNPs that have been found in the gene encoding the drug-metabolizing protein of the present invention. SNPs were identified at 17 different nucleotide positions. Some of these SNPs may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 17 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel drug-metabolizing protein of the present invention is located on a genome component that has been mapped to human chromosome 4 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the drug-metabolizing proteins of the present invention are expressed in humans in the kidney (including kidney hypemephromas), liver (including HepG2 cell lines and hepatocellular carcinomas), and pigmental retinal epithelium, as indicated by virtual northern blot analysis. In addition, PCR-based tissue screening panels indicate expression in human fetal liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in drug-metabolizing enzyme protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a drug-metabolizing enzyme protein, such as by measuring a level of a drug-metabolizing enzyme-encoding nucleic acid in a sample of cells from a subject e.g., mRNA or genomic DNA, or determining if a drug-metabolizing enzyme gene has been mutated. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver.

Nucleic acid expression assays are useful for drug screening to identify compounds that modulate drug-metabolizing enzyme nucleic acid expression.

The invention thus provides a method for identifying a compound that can be used to treat a disorder associated with nucleic acid expression of the drug-metabolizing enzyme gene, particularly biological and pathological processes that are mediated by the drug-metabolizing enzyme in cells and tissues that express it. Experimental data as provided in FIG. 1 indicates expression in humans in the kidney (including kidney hypernephromas), liver (including fetal liver, HepG2 cell lines, and hepatocellular carcinomas), and pigmental retinal epithelium. The method typically includes assaying the ability of the compound to modulate the expression of the drug-metabolizing enzyme nucleic acid and thus identifying a compound that can be used to treat a disorder characterized by undesired drug-metabolizing enzyme nucleic acid expression. The assays can be performed in cell-based and cell-free systems. Cell-based assays include cells naturally expressing the drug-metabolizing enzyme nucleic acid or recombinant cells genetically engineered to express specific nucleic acid sequences.

Thus, modulators of drug-metabolizing enzyme gene expression can be identified in a method wherein a cell is contacted with a candidate compound and the expression of mRNA determined. The level of expression of drug-metabolizing enzyme mRNA in the presence of the candidate compound is compared to the level of expression of drug-metabolizing enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate drug-metabolizing enzyme nucleic acid expression in cells and tissues that express the drug-metabolizing enzyme. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver. Modulation includes both up-regulation (i.e. activation or agonization) or down-regulation (suppression or antagonization) or nucleic acid expression.

Alternatively, a modulator for drug-metabolizing enzyme nucleic acid expression can be a small molecule or drug identified using the screening assays described herein as long as the drug or small molecule inhibits the drug-metabolizing enzyme nucleic acid expression in the cells and tissues that express the protein. Experimental data as provided in FIG. 1 indicates expression in humans in the kidney (including kidney hypernephromas), liver (including fetal liver, HepG2 cell lines, and hepatocellular carcinomas), and pigmental retinal epithelium.

The nucleic acid molecules are also useful for monitoring the effectiveness of modulating compounds on the expression or activity of the drug-metabolizing enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in drug-metabolizing enzyme nucleic acid expression, and particularly in qualitative changes that lead to pathology. The nucleic acid molecules can be used to detect mutations in drug-metabolizing enzyme genes and gene expression products such as mRNA. The nucleic acid molecules can be used as hybridization probes to detect naturally occurring genetic mutations in the drug-metabolizing enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the drug-metabolizing enzyme gene associated with a dysfunction provides a diagnostic tool for an active disease or susceptibility to disease when the disease results from overexpression, underexpression, or altered expression of a drug-metabolizing enzyme protein.

Individuals carrying mutations in the drug-metabolizing enzyme gene can be detected at the nucleic acid level by a variety of techniques. FIG. 3 provides information on SNPs that have been found in the gene encoding the drug-metabolizing protein of the present invention. SNPs were identified at 17 different nucleotide positions. Some of these SNPs may affect control/regulatory elements. The gene encoding the novel drug-metabolizing protein of the present invention is located on a genome component that has been mapped to human chromosome 4 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a drug-metabolizing enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant drug-metabolizing enzyme gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 21 7:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the drug-metabolizing enzyme gene in an individual in order to select an appropriate compound or dosage regimen for treatment. FIG. 3 provides information on SNPs that have been found in the gene encoding the drug-metabolizing protein of the present invention. SNPs were identified at 17 different nucleotide positions. Some of these SNPs may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control drug-metabolizing enzyme gene expression in cells, tissues, and organisms. A DNA antisense nucleic acid molecule is designed to be complementary to a region of the gene involved in transcription, preventing transcription and hence production of drug-metabolizing enzyme protein. An antisense RNA or DNA nucleic acid molecule would hybridize to the mRNA and thus block translation of mRNA into drug-metabolizing enzyme protein.

Alternatively, a class of antisense molecules can be used to inactivate mRNA in order to decrease expression of drug-metabolizing enzyme nucleic acid. Accordingly, these molecules can treat a disorder characterized by abnormal or undesired drug-metabolizing enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the drug-metabolizing enzyme protein, such as substrate binding.

The nucleic acid molecules also provide vectors for gene therapy in patients containing cells that are aberrant in drug-metabolizing enzyme gene expression. Thus, recombinant cells, which include the patient's cells that have been engineered ex vivo and returned to the patient, are introduced into an individual where the cells produce the desired drug-metabolizing enzyme protein to treat the individual.

The invention also encompasses kits for detecting the presence of a drug-metabolizing enzyme nucleic acid in a biological sample. Experimental data as provided in FIG. 1 indicates that the drug-metabolizing proteins of the present invention are expressed in humans in the kidney (including kidney hypernephromas), liver (including HepG2 cell lines and hepatocellular carcinomas), and pigmental retinal epithelium, as indicated by virtual northern blot analysis. In addition, PCR-based tissue screening panels indicate expression in human fetal liver. For example, the kit can comprise reagents such as a labeled or labelable nucleic acid or agent capable of detecting drug-metabolizing enzyme nucleic acid in a biological sample; means for determining the amount of drug-metabolizing enzyme nucleic acid in the sample; and means for comparing the amount of drug-metabolizing enzyme nucleic acid in the sample with a standard. The compound or agent can be packaged in a suitable container. The kit can further comprise instructions for using the kit to detect drug-metabolizing enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the drug-metabolizing enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the drug-metabolizing enzyme gene of the present invention. FIG. 3 provides information on SNPs that have been found in the gene encoding the drug-metabolizing protein of the present invention. SNPs were identified at 17 different nucleotide positions. Some of these SNPs may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified drug-metabolizing enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage X, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology. Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., S. cerevisiae include pYepSec1 (Baldari, et al., *EMBO J* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. Nature 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a drug-metabolizing enzyme protein or peptide that can be further purified to produce desired amounts of drug-metabolizing enzyme protein or fragments. Thus, host cells containing expression vectors are useful for peptide production.

Host cells are also useful for conducting cell-based assays involving the drug-metabolizing enzyme protein or drug-metabolizing enzyme protein fragments, such as those described above as well as other formats known in the art. Thus, a recombinant host cell expressing a native drug-metabolizing enzyme protein is useful for assaying compounds that stimulate or inhibit drug-metabolizing enzyme protein function.

Host cells are also useful for identifying drug-metabolizing enzyme protein mutants in which these functions are affected. If the mutants naturally occur and give rise to a pathology, host cells containing the mutations are useful to assay compounds that have a desired effect on the mutant drug-metabolizing enzyme protein (for example, stimulating or inhibiting function) which may not be indicated by their effect on the native drug-metabolizing enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a drug-metabolizing enzyme protein and identifying and evaluating modulators of drug-metabolizing enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the drug-metabolizing enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the drug-metabolizing enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S. cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, drug-metabolizing enzyme protein activation, and signal transduction, may not be evident from in vitro cell-free or cell-based assays. Accordingly, it is useful to provide non-human transgenic animals to assay in vivo drug-metabolizing enzyme protein function, including substrate interaction, the effect of specific mutant drug-metabolizing enzyme proteins on drug-metabolizing enzyme protein function and substrate interaction, and the effect of chimeric drug-metabolizing enzyme proteins. It is also possible to assess the effect of null mutations, that is mutations that substantially or completely eliminate one or more drug-metabolizing enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. A nucleic acid vector comprising the nucleic acid molecule of SEQ ID NO: 1 or SEQ ID NO: 3.

2. A host cell containing the vector of claim 1.

3. A process for producing a polypeptide comprising SEQ ID NO: 2, the process comprising culturing the host cell of claim 2 under conditions sufficient for the production of said polypeptide, and recovering said polypeptide from the host cell.

4. An isolated polynucleotide consisting of a nucleotide sequence set forth in SEQ ID NO: 1.

5. An isolated polynucleotide consisting of a nucleotide sequence set forth in SEQ ID NO: 3.

6. A vector according to claim 1, wherein said vector is selected from the group consisting of a plasmid, virus, and bacteriophage.

7. A vector according to claim 1, wherein said isolated nucleic acid molecule is inserted into said vector in proper orientation and correct reading frame such that the protein of SEQ ID NO: 2 may be expressed by a cell transformed with said vector.

8. A vector according to claim 7, wherein said isolated nucleic acid molecule is operatively linked to a promoter sequence.

9. An isolated nucleic acid molecule consisting of a nucleotide sequence that is completely complementary to a nucleotide sequence consisting of SEQ ID NO: 1 or SEQ ID NO: 3.

10. An isolated polynucleotide comprising a nucleotide sequence set forth in SEQ ID NO: 1.

11. An isolated polynucleotide comprising a nucleotide sequence set forth in SEQ ID NO: 3.

12. An isolated nucleic acid molecule consisting of a nucleotide sequence that is completely complementary to a nucleotide sequence comprising SEQ ID NO: 1 or SEQ ID NO: 3.

* * * * *

SEQUENCE LISTING

<160> NUMBER OF SEQ ID NOS: 5

<210> SEQ ID NO 1
<211> LENGTH: 2759
<212> TYPE: DNA
<213> ORGANISM: Human

<400> SEQUENCE: 1

```
caaccattgc agatcagtgt gtgagggaac tgccatcatg aggtctgaca agtcagcttt      60
ggtatttctg ctcctgcagc tcttctgtgt tggctgtgga ttctgtggga aagtcctggt     120
gtggccctgt gacatgagcc attggcttaa tgtcaaggtc attctagaag agctcatagt     180
gagaggccat gaggtaacag tattgactca ctcaaagcct tcgttaattg actacaggaa     240
gccttctgca ttgaaatttg aggtggtcca tatgccacag gacagaacag aagaaaatga     300
aatatttgtt gacctagctc tgaatgtctt gccaggctta tcaacctggc aatcagttat     360
aaaattaaat gatttttttg ttgaaataag aggaacttta aaaatgatgt gtgagagctt     420
tatctacaat cagacgctta tgaagaagct acaggaaacc aactacgatg taatgcttat     480
agaccctgtg attccctgtg gagacctgat ggctgagttg cttgcagtcc cttttgtgct     540
cacacttaga atttctgtag gaggcaatat ggagcgaagc tgtgggaaac ttccagctcc     600
actttcctat gtacctgtgc ctatgacagg actaacagac agaatgacct ttctggaaag     660
agtaaaaaat tcaatgcttt cagttttgtt ccacttctgg attcaggatt acgactatca     720
tttttgggaa gagtttttata gtaaggcatt aggaaggccc actacattat gtgagactgt     780
gggaaaagct gagatatggc taatacgaac atattgggat tttgaatttc ctcaaccata     840
ccaacctaac tttgagtttg ttggaggatt gcactgtaaa cctgccaaag ctttgcctaa     900
ggaaatggaa aattttgtcc agagttcagg ggaagatggt attgtggtgt tttctctggg     960
gtcactgttt caaaatgtta cagaagaaaa ggctaatatc attgcttcag cccttgccca    1020
gatcccacag aaggtgttat ggaggtacaa aggaaaaaaa ccatccacat taggagccaa    1080
tactcggctg tatgattgga taccccagaa tgatcttctt ggtcatccca aaaccaaagc    1140
ttttatcact catggtggaa tgaatgggat ctatgaagct atttaccatg gggtccctat    1200
ggtgggagtt cccatatttg gtgatcagct tgataacata gctcacatga aggccaaagg    1260
agcagctgta gaaataaact tcaaaactat gacaagcgaa gatttactga gggctttgag    1320
aacagtcatt accgattcct cttataaaga gaatgctatg agattatcaa gaattcacca    1380
tgatcaacct gtaaagcccc tagatcgagc agtcttctgg atcgagtttg tcatgcgcca    1440
caaaggagcc aagcacctgc gatcagctgc ccatgacctc acctggttcc agcactactc    1500
tatagatgtg attgggttcc tgctgacctg tgtggcaact gctatattct tgttcacaaa    1560
atgtttttta ttttcctgtc aaaaatttaa taaaactaga aagatagaaa agagggaata    1620
gatctttcca aattcaagaa agacctgatg gggtaatcct gttaattcca gccacataga    1680
atttggtgaa aaccttgcta ttttcatatt atctattctg ttatttttatc ttagctatat    1740
agcctagaat tccatgatca tgaggttgtg agtatatctc attctttcgt tgcattttcc    1800
```

-continued

```
taggtgtgct tactctcttc tctcactttg tgacacaagg acatgaatac atctaaattt    1860
tcctatttct gatatcactg tttccatgac gtcattactt ctctaacctt aagtgatagg    1920
gtgacctgca atatgctgat tcctggtgtt tgcacaaaca catggatgta agaagtaaa     1980
aaatgtaaaa ttcacaaaat tcagtaaacc acacaaatca atgaagcatt ctatgacatt    2040
agcttgttat gagtaacata atgattttc ttttcaatt taaataagcc cttctacata      2100
cccagcatta ctgatctcag acaatgaatt gctaaaaatg acgatagggc attacactca    2160
gaatagtttg ctatatttcc acatacctca tctagatgtc atagcctaca tttctgccat    2220
cacttaactg acattttttg tgtgttcttg atgataaata gacagttctt attattgtcc    2280
tcaaataata aaagaaactg aaattttctt acatagagaa aatgtccata agatattcaa    2340
gttaaacaga ttattttgag ataagtaacc attagaaata tgtgattgta atttctgatt    2400
ttataaaatt ttaattgata gtacacttga tttaaatgtc tattctttaa aatgatgaat    2460
actcataatt cttatctcta taatcaaaag tataatttac tgtagaaaaa taaagagatg    2520
cttgttctga agtaaaaaa aaaaaaaaa aaaacactgt catgccgtta cgtagcgtat      2580
cgttgacagc ccactgtcat gccgttacgt agcatatcgt tgacagcgac actgtcatgc    2640
cgttacgtag cgtatcgttg acagcactgt catgcgttac gagcgtatcg ttgacagcac    2700
tgtcatgccg ttacgtagcg tatcgttgac agcaaaacac tgtcagccgt tacgtagcg    2759
```

<210> SEQ ID NO 2
<211> LENGTH: 527
<212> TYPE: PRT
<213> ORGANISM: Human

<400> SEQUENCE: 2

```
Met Arg Ser Asp Lys Ser Ala Leu Val Phe Leu Leu Gln Leu Phe
  1               5                  10                  15

Cys Val Gly Cys Gly Phe Cys Gly Lys Val Leu Val Trp Pro Cys Asp
                 20                  25                  30

Met Ser His Trp Leu Asn Val Lys Val Ile Leu Glu Glu Leu Ile Val
             35                  40                  45

Arg Gly His Glu Val Thr Val Leu Thr His Ser Lys Pro Ser Leu Ile
         50                  55                  60

Asp Tyr Arg Lys Pro Ser Ala Leu Lys Phe Glu Val Val His Met Pro
65                  70                  75                  80

Gln Asp Arg Thr Glu Glu Asn Glu Ile Phe Val Asp Leu Ala Leu Asn
                 85                  90                  95

Val Leu Pro Gly Leu Ser Thr Trp Gln Ser Val Ile Lys Leu Asn Asp
            100                 105                 110

Phe Phe Val Glu Ile Arg Gly Thr Leu Lys Met Met Cys Glu Ser Phe
        115                 120                 125

Ile Tyr Asn Gln Thr Leu Met Lys Lys Leu Gln Glu Thr Asn Tyr Asp
    130                 135                 140

Val Met Leu Ile Asp Pro Val Ile Pro Cys Gly Asp Leu Met Ala Glu
145                 150                 155                 160

Leu Leu Ala Val Pro Phe Val Leu Thr Leu Arg Ile Ser Val Gly Gly
                165                 170                 175

Asn Met Glu Arg Ser Cys Gly Lys Leu Pro Ala Pro Leu Ser Tyr Val
            180                 185                 190

Pro Val Pro Met Thr Gly Leu Thr Asp Arg Met Thr Phe Leu Glu Arg
        195                 200                 205
```

-continued

Val Lys Asn Ser Met Leu Ser Val Leu Phe His Phe Trp Ile Gln Asp
    210                 215                 220

Tyr Asp Tyr His Phe Trp Glu Glu Phe Tyr Ser Lys Ala Leu Gly Arg
225                 230                 235                 240

Pro Thr Thr Leu Cys Glu Thr Val Gly Lys Ala Glu Ile Trp Leu Ile
                245                 250                 255

Arg Thr Tyr Trp Asp Phe Glu Phe Pro Gln Pro Tyr Gln Pro Asn Phe
            260                 265                 270

Glu Phe Val Gly Gly Leu His Cys Lys Pro Ala Lys Ala Leu Pro Lys
        275                 280                 285

Glu Met Glu Asn Phe Val Gln Ser Ser Gly Glu Asp Gly Ile Val Val
    290                 295                 300

Phe Ser Leu Gly Ser Leu Phe Gln Asn Val Thr Glu Glu Lys Ala Asn
305                 310                 315                 320

Ile Ile Ala Ser Ala Leu Ala Gln Ile Pro Gln Lys Val Leu Trp Arg
                325                 330                 335

Tyr Lys Gly Lys Lys Pro Ser Thr Leu Gly Ala Asn Thr Arg Leu Tyr
            340                 345                 350

Asp Trp Ile Pro Gln Asn Asp Leu Leu Gly His Pro Lys Thr Lys Ala
        355                 360                 365

Phe Ile Thr His Gly Gly Met Asn Gly Ile Tyr Glu Ala Ile Tyr His
    370                 375                 380

Gly Val Pro Met Val Gly Val Pro Ile Phe Gly Asp Gln Leu Asp Asn
385                 390                 395                 400

Ile Ala His Met Lys Ala Lys Gly Ala Ala Val Glu Ile Asn Phe Lys
                405                 410                 415

Thr Met Thr Ser Glu Asp Leu Leu Arg Ala Leu Arg Thr Val Ile Thr
            420                 425                 430

Asp Ser Ser Tyr Lys Glu Asn Ala Met Arg Leu Ser Arg Ile His His
        435                 440                 445

Asp Gln Pro Val Lys Pro Leu Asp Arg Ala Val Phe Trp Ile Glu Phe
    450                 455                 460

Val Met Arg His Lys Gly Ala Lys His Leu Arg Ser Ala Ala His Asp
465                 470                 475                 480

Leu Thr Trp Phe Gln His Tyr Ser Ile Asp Val Ile Gly Phe Leu Leu
                485                 490                 495

Thr Cys Val Ala Thr Ala Ile Phe Leu Phe Thr Lys Cys Phe Leu Phe
            500                 505                 510

Ser Cys Gln Lys Phe Asn Lys Thr Arg Lys Ile Glu Lys Arg Glu
        515                 520                 525

<210> SEQ ID NO 3
<211> LENGTH: 21000
<212> TYPE: DNA
<213> ORGANISM: Human
<220> FEATURE:
<221> NAME/KEY: misc_feature
<222> LOCATION: (1)...(21000)
<223> OTHER INFORMATION: n = A,T,C or G

<400> SEQUENCE: 3
ttctagaggg ttggaacaac ttttccctga tacattgcat ttttttgata ccttcagtac    60
atgttaaact ggcaaccacc agtgaacttt actcttaaaa tattaatttt taacttctgt   120
gcttatattg tcatttcaac tccttgctta gtaactacaa aaccattgca gatcagtgtg   180
tgagggaact gccatcatga ggtctgacaa gtcagctttg gtatttctgc tcctgcagct   240

```
cttctgtgtt ggctgtggat tctgtgggaa agtcctggtg tggccctgtg acatgagcca    300
ttggcttaat gtcaaggtca ttctagaaga gctcatagtg agaggccatg aggtaacagt    360
attgactcac tcaaagcctt cgttaattga ctacaggaag ccttctgcat gaaatttga     420 ggtggtccat atgccacagg acagaacaga agaaaatgaa atatttgttg acctagctct    480
gaatgtcttg ccaggcttat caacctggca atcagttata aaattaaatg attttttttgt   540 tgaaataaga ggaactttaa aaatgatgtg tgagagcttt atctacaatc agacacttat    600
gaagaagcta caggaaacca actacgatgt aacgcttata gaccctgtga ttccccgtgg    660
agacctgatg gctgagttgc ttccagtccc ttttgtgctc acacttagaa cttctctaag    720
aggcaatatg gagcgaagct gtgggaaact tccagctcca ctttcctatg tacctgtgcc    780
tatgacagga ctaacagaca gaatgacctt tctggaaaga gtaaaaaatt caatgctttc    840
agttttgttc cacttctgga ttcaggatta cgactatcat ttttgggaag agttttatag    900
taaggcatta ggtaagacac ttttgttttta tttttaattt agttatcaaa agaaatattt   960
ttaaaaattg tcatacattg tctatgacat atatatgcag gtcaatgagt tttttttagaa  1020 aatgttgtag ctgttttttca taagaaagt gtatttgttc taagcgtaag ataacctact   1080
ttcttaatac cagtaatata cttaaaaatg atcatcaata actaagagat tatattttgt   1140
atttcctcca aatagcgcaa atcaacatca catattttttg agaatcactg attgttagtc  1200
tgaatgttat agaatttcta ttgaaataaa atgctaatca ttattttctc tctcatcatg   1260
tatttaagaa aatcttcaga aggtcttctt tgaattaatt tttcaagagt cattaaattg   1320
aacattttct agaattcttt aatttcttag gtgattactt cacaaaaact tgaaaaaata   1380
ttataaaaag ttaaaaaact tacggtcttg tggggcataa gatagtagaa ttttttacttt 1440 actgatatac acctatttga cttattttta tttctttgct ttactgataa aaagttgttt   1500
tgctttgcaa ttttcatata gttgtgatca gagctggtca atgcaagaca tgtttttatc   1560
caaatatgtt tgagaattat gtagaaacat gaaaaaaggt acaattatat ccgacactaa   1620
aatattgttt aatgtattcc aacgaattct tatgcataga ctgtttcaca gaactaatat   1680
tcagaggatc ccagttcaaa tgtccttagc cttagacatg atttgaattt acatatattg   1740 atttgctttta aataatttttc cattcagtaa gctgtgccta gctgcagata gcctaccagg   1800
ctttatggat ctaggtaaac aatacaaatc tcttggcctc aagtctacat tcagatatta   1860
atttaaaggg gtacagctat atagaggtca ctggcaaatt ttggtaaaat aggattatag   1920
taaaagcccc ctgacaagat tgaaatttaa aataaaacaa aagtgttatc aaagggtga    1980 aagagcattt tccaataaac aaaagtgggt tctggccatg cattcagaaa ttccccaaca   2040 attcttaaa aatcatggag cagcttgata tataagaaat tcatttaata actatatta     2100 ttatgtagct ccaacttact aaattattga ttattatata tttttagaa ttatctattg    2160 tgagtctaaa tcaagagtat atattcaaac aactatagga aaagggatat cagtcaattt   2220
caattcaagg atttatttcc ataagtgctt acgcacaggt gtatttcatt ttattataca   2280
ttgctttatt gtccttcaca aaaattgcaa tttacaaatt aaaggttttt gaaaaccttg   2340
aatcaagcta atcaattttgg cgtaatattt ccaacaacaa gtgtgtactt ttgactctat  2400
cacatattgg catttatcat gcttttttcaa atttttcatt gttatatctg ttacggtgat  2460
ctgggatcag tgttccttga tggttacacg tttattagct tggggggcacc ttgatgtgtt  2520 acaatataag acagcaaact taattataaa tgttgtgcat gtactaactg ctccgctgat   2580
```

```
tcgtttcccc atcccacttc ttcttaggcc tccctattcc ctgagacaca gtaatataac    2640
atacaatgac ttctaaatgt tccagtgaaa agaaaagtag caggtctctc aatttaaacc    2700
aaaaatataa aggaataagt ttaatgagta ctatagttta gatatggttt gcttgaccct    2760
acaaaatcct gtgttgaaat ttgatcacca atattggagg tggggcttga tgggaagtgt    2820
tagggtcatg agggtagatt ccttatgagt acattaatgc tctccctggg gaaatgggtg    2880
agttcgttct cactctatta ggtcccagga gagataatta ttaaaaagag ccaggaacat    2940
ccaccttctt tctcttgcat atctctcatt atctgatccc tgcacttgct ggctcccaac    3000
atcttcttca atgagtggag gaaaccagag gtcttcacca gacacagatg ttggtgccat    3060
gcctcttgta taccctgaag aattgtgagc caaataaaaa ccttttttctt ttacaaatta    3120 gacagcctca gttattcctt tgtagcaaca aaaaagcct gggacaggcc aaaaactaca     3180
ccattgcacc aaacagttaa acaagatgtg agtgcaaagg aaagttttt ggaggaaatt     3240 aaaagtgcta ctccagtgta catacaaatg ataagaacaa ataaccatta tcagtgctga    3300
tatggagaaa attttagttg tctggagaga aaatcaaatt agctagccag ctgcagtgat    3360
tcatatctgt aatcccagta acttgggagg ctcaggtggg agaacggctt gagcccagaa    3420
gtttgaagtc caaggctgca gtgagctatg attgctccac tgcactccaa cctaggtgat    3480
agagcaaaac cactaccaaa aaaaaaaaaa aaaaaagaa gaaaagaaa agaaaaaaaa      3540 ttaaaccaac cacaacatca ccttaggttt tggcattagc taaaaactaa tacatagtaa    3600
agcgttaact attcaattgc atgaaacctc agagaggaga ggaagatgca gaaaaaaga    3660 ctgaagctag tagaggttga ctaatgaggt ttacaggaat aaactgccta catgatgcaa    3720
aagttcaatg tgaagcaata ggaagtcatg cagaagactt agctaatata ctcagtaaat    3780
gtggctacag taaacaaatg atttcaatg tagacctaac agccttctgt tggaagaaga    3840
tgccatttaa aactttcata gctagagaag agaagtcaat gcttgtctct gaagctacaa    3900
aaaacaggct gaatctcttg tagtggctaa tgcagctgat gacaaaggta aagccaatgc    3960
ccatttactt tttgtaataa ttatagagga ctcttaataa ttatgttaaa tctactttgc    4020
ctgtgttata tcaatggaac aacaaagcct ggatgatatc acattggtat atgacatggc    4080
ttattgaata ttttaagcac actgttgaga cctattgctc aaaaaagagg attcctttca    4140
aaatattgct gctcattgac aattcacatg gtcaacaaag ggctctgatt aagatgtaca    4200
gatattaatg tttgcctgct tgctattatt acatccatct tacatgccat ggatcatata    4260
gccttgactt tcaagtctta tgtaagaaat atattttgta aggctatagc tcttactaat    4320
ggggaaagta tattgaaaac cttttcaaaa ggattttca ttctagattc cattaagaac     4380
attcatggtt catgagagga agtcaagata ttaacattaa caagagtttg gaaaaatttt    4440
gattctaact ctcctggatg attttgaggg attgaagaca tcatgtgaag aattaactgg    4500
ggatggggtg gtcatgaaaa ataaataga attataagtg ggcctgaagg tttgtctaaa     4560
ttgctataat atcatgataa aactaaaacc tgtaaaaccg gtgaggaggt gcttttaaa     4620 cagttactt ttatagatga acacagaaat tggttttgtg agttggaatc ttctccgagt     4680
gaaaatgcta tgaacattgt tgaaatggct acaaatgact tagaatatta cacaaaatta    4740
gtagataagg cagcatcaag gtttgagaga atggactcaa attttgaaag aaattctact    4800
atgggtaaac tgctgtgaaa catcatcata tgctacagag aaatctttca tgaaaagatg    4860
agtcaattca tgcaacaatc tttgttgtct aattttaaaa attgtccagc tgccctgatc    4920
aatcaacagt aatcagcact gaggcaagac cctacaccag aaaaaataaa aataaaaaac    4980
```

```
ctcacttgct gaagactcag cttattatta gcacttttta gccatacttt taactaaggt    5040
atgtgcattc cttttaaac gtgatgatat tgcacagcta atagcctaca aggtatggtt     5100
aacataactt ttatatgtcc tgggacccaa atttgtgtga atcactttat tgacatattc    5160
cttttattga gatgaactgc aacttatctt gcaatatctc caagatatgt gtgtatggca    5220
tttcaaataa gatgtgaaat tattttatta gtataaaaag caaatttaat tttctttcct    5280
ttgatcatct ttatccttgt tactgtgtat ttatccttta aacattgaat gactccaatt    5340
gtttaaaact gagtctttct taaatgagtc ctaatatcat agtaattaaa atcacctaca    5400
agttggtaat gcaggcagca tgtgaggcac agaaaacaac aaatttataa gacataaatg    5460
catttgcttg gaagctgaga gaaggctcta ttctaatttc tgataacttc aaactgagta    5520
tcttcagtaa aatttattca ctatcaaatt caaggcgttt ggatttatga cctaggaaaa    5580
aacttcaaac attaaaatgt gatgacctta aaaagaggct ctccacacta tggtgtataa    5640
caccaccaac tttgattaga attttaaaga gaaacaaatt ctcttatgga gtttatcttt    5700
ttatcacttg caaaatatgt ttttgtaaag agatactaat tacttagtta tttgtagtta    5760
gccattcttc tgattaaaaa cctaaaatta aatcttgaaa atgtgttttc cttcaaaaca    5820
catcatttga gagaaacact aaagtaagtg tatgattatc atagcatgta cataggtgct    5880
tcacaaccca aaaagaatat tgtcatgggt aagaatcagt aaaggaattt ctcctaataa    5940
aacagtagcc tattaattaa agtaatgata tgcaatacag caagttaaag ggaactgatc    6000
ctggtgggat tattgaaaga tatacccttg actatagatt agaaaataca gagatgttat    6060
ttagtgaaga tattgtggta ctcatttatc atctgcaatt cacttgcaga ggaaaaaatg    6120
agtaataaat tcatttgcat tttggatttg tgtctttaag ttgtgaaaat acacttaaat    6180
ataaccatct gtcctttgct ccttccttcc ttccttcttt ccttccttcc ttccttcttt    6240
ccatccttcc ctccctccat ccttccttcc ttcctttctt cctttcctcc tttctttctc    6300
tgtccttcct tcttttttcc tttctttctt ttttcttctt tattatttca ttaattcccc    6360
cttccatttg acgtctaaaa gccatgttgt tctagaggac ttaaactttt ttttttctta    6420
atagcttact gaaaaattag tgatacaatt ttttatttga attgtatgct aattcattct    6480
gttatttctt ttattgagga aggcccacta cattatgtga gactgtggga aaagctgaga    6540
tatggctaat acgaacatat tgggattttg aatttcctca accataccaa cctaactttg    6600
agtttgttgg aggattgcac tgtaaacctg ccaaagcttt gcctaaggta ggactattgt    6660
attaaggaat attatgtact ttatgacatg acttgttttc ccttgaaaga ttacaacctt    6720
agttatagaa ggatgatgtt gaatgtcgtc tgtttgcagc tccatattta ttttccatgc    6780
cacagggct cttataggtg attatatgtc ttttcggtat tatattgaga aagtaggcag     6840
aagaatttca tgattagaat agattttaaa atactagtat tacaatagtt tggataataa    6900
attgaattaa tagggaattg gagccatgaa gatcactaaa aagaatgctc tagcctttct    6960
cacaatcaaa ttgggcttat gaacaaggat atttgtcatg atagtacaga aataagcata    7020
ttttcatgag acatattgga tatattccac aggagttggt gagtgagaga aaataagtga    7080
tgaaggaaga caaagaataa aagaaatttc aataaatgg aaagtttaag tgtttaatga     7140
tagtgatgac ttttactcaa ataagtgctt agaagtcatc ttgtttgtga tttatatgat    7200
gaattctgtg ttgtgactat ccactttgag ctcgtgagaa tgttaggtga ggtttaataa    7260
aagccatttg agaaaaacaa ggtttcaacc tctgtggaca gaaatctaaa tatcgatagt    7320
```

| | |
|---|---|
| tatcaggaca aagtagagct catagaaata attttgcagc ctgcaggttt gttttggagt | 7380 |
| gaaaataaaa ttgtatacta tattcctaaa tcatcagagg aaaaaattta tagttcaagg | 7440 |
| aatgttgaaa gaaacaatat tgagaagtaa aagtgagtaa tagttgttat agttttttaa | 7500 |
| tagttttgta agtatgtctt gagttcactg tcccaaaagt ggctattagc tctagccttg | 7560 |
| acctgacaag gttctaggat atttagtcat ggatgttcat aatctacctc ttacgggata | 7620 |
| cttttttattc tgatgaacag cctaatgcct aagtgtgcaa tctataccaa gattgttctt | 7680 |
| atagggaact tgtttacact ggaagacacc actgtgtctc ttgtatgacc tatgtcttct | 7740 |
| ttatccctac aaaggtaacc acattatagg aaaccctgac aaggccagat gttatatttg | 7800 |
| tgttggtcaa gtgagaaaac atgggagaaa cttaaccaaa cacataaaat aacagaaaca | 7860 |
| gtcttctttg accatttcta gagaaaagag ttcagcatcc cttgtaaggc cactaggaag | 7920 |
| aagaaaattc tctgggaaaa gcacattcaa ccaatgaatg gagaccaaga aagagagtga | 7980 |
| gggatctatg tgccaaaatg ttaactggga tccagggtgt tacctaggtg ggtttccaat | 8040 |
| ggggaactgt aattggtagg tttaatgcaa gcaggcacaa agtccatgga ggcattctga | 8100 |
| gactgaaaga tagtcacttt ggcatatctg cacagaatct gatcagtgat tcaagcccaa | 8160 |
| gtaggctgta tctagttgtc ctataggggtg gttaccagga ggcagtgtgt aagtaaaaat | 8220 |
| cctgactgaa cacattgagg aaatggaagg aggtggaaga ttttaaacgg tgtcagtgtt | 8280 |
| gactaagacc tgcttctggt atggaaaatt caacttatat tttaaatgca tagccagaca | 8340 |
| acataaaatt ataagaattt accacaatag ctatggtaac aatactgggt ttacctatta | 8400 |
| ctacagagtg aaaagaaaac cctcatttcc cattttatgg aaatataatc aaaatcctat | 8460 |
| aaggaaggtt tcagagccag taggatttcc agaaaaatta ttggttttat agtaagatgt | 8520 |
| gtattgatga atataatttt atttattaat tattaatatc actttactta ccaggaaagt | 8580 |
| tataccagaa aaccaagctc tcttaagcca tggcatctgt atctaaaata gaaatacaga | 8640 |
| aggagagctg acaatttcca tcattctcta ggtaatctcc catgccattc tacccttat | 8700 |
| tcccacactc ccagttttac acacacacac aaacacacac acacaaacac acactcatag | 8760 |
| aaataatcat agaagacata ttttttaaaaa agttagatcc atacagtaat aatttattag | 8820 |
| gtaaaagctt ttgtgctgat aattttacaa gtttaattga gatatatttt agggctgtct | 8880 |
| tacactaaat atttatttt attttttaaa tttgacatgt aataattgca catgtttaag | 8940 |
| agaaatgctg tggtattaca atacatttaa atgttgtgta ataattacat caagataata | 9000 |
| aacccatcat ctaaatattt atcatttctt tgtggtgata acattcaaaa acctcctttc | 9060 |
| tggctatctt gaaatatgta atacattact attaactata gttacccaac aacttaatat | 9120 |
| aataacagaa catattcttc caaatttaaa cgttgtatcc attgatccac catttctcat | 9180 |
| tgccctccct actatctctt cagcctctag taaccacaat tctactctct aattatatta | 9240 |
| tgaatgcatt ttttgattcc acatataagg gataccatgc tatctctgcc tggattattt | 9300 |
| cagttaacat tatgccctgg aggttcattc atgtttctac aaatgacagg atttcattct | 9360 |
| tttttttcca atatatattt aatgaaatgg atatatataa acattggaaa atgtatatat | 9420 |
| atatatatat ctccagtgga atgctattga gctataaaaa agttaatata taatagaaat | 9480 |
| aaagcttata tatctctaat ggaatggata tatatata atggaataga aatatatatc | 9540 |
| tatacatata aacacacgca atatacatat ccatttcatt gcatatatat atatatagag | 9600 |
| agagagagag agagatattt tcaaatgtgt gtatatatat ccaatggaat ggacatatat | 9660 |
| atatgtatat ttttttccata ttttcttttat gtatttcttc attaatggat gtttaggttg | 9720 |

-continued

```
attcatccct tgggtatatg aataatgttg atgtaaacat agaaggacag atatctctat    9780
gacttcttag tttatttaaa tatacaccca gtaatggaaa tgctgtataa tatggtagtt    9840
ctattttcat tttttgagga actaccatac cgttttcctt actaattgta ctaatttgca    9900
tttccctcaa cagtttataa aagatcttct ttctctgcat actttctagc acttgttatt    9960
tttgcctttt gataatagcc ataacagggg tgatgtgata tctcattgta gttttgatt   10020
gcatttccct gatgattagt gattttgagc attttgtaat tatacttctt agtcactgat   10080
agtcttcttt tgagaagtgt ctattcaggt cttttgctta ttttttaatc aaattagtaa   10140
tttattttta ttgactgatg tgacttctat gtatatttga gatagtaact tattgtcaga   10200
ttcatagttt gcaaatattt ttcatgttgt gaattgtctc ttcaccctgt tgtttgcttc   10260
attttctctg cacaagctca atgctttgat ataacccatt tatctacttt tccttttgtt   10320
ggctgtgctt ctgaagtcct atccaaaaaa atccttgcct agaccaatgt cacaaatcat   10380
tcctcctaca gtttcttcta gtagttgtat aatgtttggc cttatattta actttgtaat   10440
tcattttttac ttactttgta tatggtgagg gatagaggtc tagtttcatt ttctgcatgt   10500
ggatatgcag ttttcctagc accatttagt gaagaggttg ccttttttct attatgtgtt   10560
cttggcacct ttgtcaaaag tcagttagct gctatattcc tccatttgtg ttgttataga   10620
ggaacacatg agactagcaa atttatatat caaatagaat tatttgaatg atagttctgc   10680
atactgtaca agaagcacag cactgacttc tgcttggcct ctggtaaggt tctcaagatg   10740
cttccacttg tggtagaagg caaacatgag ctggtatatg caaaggtctc atgacaagag   10800
aggaaaccat aaagagggga tgtgagggag tgccaggttt tgtaaaacaa ctagctcttc   10860
tgggaactaa tagagtaaaa attcgcctcc caggcagggg attaatctat tcatgaggga   10920
tctgcttcca tgacaaaggc acattctgtt agattctacc cccaatattg gggatcaaat   10980
tttaacatga agtgtggagg gctcaaatat ccatactatg gcagcagtaa atgcataaat   11040
ttattttgtg gatctctatt ctatatagta ttggtgtatg tatctgtttt catgccactg   11100
ccatactgtt ttggtgatga tatctatgct atatatgtgt gtgtgtatat atatattata   11160
tatatgtata tatgtgtata ttatatatat gtatatatgt gtatattata tatatataat   11220
actttaagtt ttatatatat ataaaatact ttaagttcaa gggtacatgt gcaggatgtg   11280
caggtcagtt acataggtat acatgtgcca ttttggtttg ctgcatgcat caactcatca   11340
ttacattagg tatttctcct aatgctatcc ctccaccagc cacccaaccc caacaggcc   11400
aggtgtgtga tgttccccgc cctgtgtcca tgtgttctca ttgttcactt cctacctaaa   11460
agtgagaaca tgcagtgttt gattttctat ccttgtgata gtttgctgag aatgactgtt   11520
ttcagcttca tccatgtccc tcaaaaggac atgaactcat cctttatttat ggctgcatag   11580
tattccatgg tgtatatgtg ctacgttttc ttaatccagt ctatcactgt tggacatttg   11640
ggttggttcc aagtctttgc tattgtgaat agtgctacaa taaccatatg tgtgcatgtg   11700
tctttatagc aacatgattt actatccttt gtgtacatac ccagtaatgg gataactggg   11760
tcaaatggta tttctagttc tagatccttg aggaatcccc acactgtctt ccacaatggt   11820
tgaactaatt tacattccca ccaacagtgt aaaaacgttc ctatttcccc acatcctctc   11880
cagtatctgt tgtttcctga ctttttaatg atggccattc taactcacat gagatggtat   11940
ctcattgtgg tttttgtttg catttctctg atgaccagtg atgatgagca ttttttcatg   12000
tgtcttttgg ctgcataaat gtcttctttt gacaagtgtc tgttcatatc ctttgcccac   12060
```

```
ttttcaatgg agttgtttgt ttttttcctg taaatttgtt taagttcatt gtagattctg    12120
gatattagcc ctttgtcaga tgggtagatt gcaaaaattt tctcccattc tgtaggttgc    12180
ctgttcaccc tgatggtagt ttcttttgct gtgcagaagc tctttagctt aattagatcc    12240
catttgtcaa tttcggcttt tgttgccatt gcttttggtg ttttagtcat gaaacccttg    12300
cccaggccta agtcctcagt ggtatagcct aggttttctt ctaggatttt tatggtttca    12360
ggtctaacat ttaagtcttt aatccatctt aaattaattt ttgtataaga tgtaagaagg    12420
gatccgtttc aactttctac atatggctag cgtgttttcc caacaccatt tattaaatag    12480
ggaatccttt ctccatttct tgattttgtc atatttgtca aacatcacat ggttagagat    12540
gtgtagtgtt atcactgagg cctcttttct gactccattg atctatatat ctgttttgat    12600
accaatacca tgttgttttc gttactgcaa ccttgtaatg caatttgaca ttcaggacca    12660
tgatgcctcc agtctctttt tttttttcta ataatttttt ttgtcaatgt aagctcattt    12720
tcgcttcttt ctgatccata agtattttt ttcccatttt gtggagaacg ccgcnnnnnn    12780
nnnnnnnnnn nnnnnnnnnn nnnnnnnnnn nnnnnnnnnn nnnnnnnnnn nnnnggcaca    12840
cctcgtgcgc atatatatat atatatatat atatacctct atatatatat acatacatac    12900
atacatacac acctccttgt ctggtgtggg atcagggtaa tgctagcctc acaagatgat    12960
actgaagtgt ttttgccttt ttgacttttt gatggtttgg aagagtgaga aaaagtgtta    13020
ttaattattc tttaaatttt gttgaatttc atagtgaaga ccttagctca ctggcttttt    13080
taatgagaac tttattactg atttaaactt cttcttcatt atttatttct gccttgtttt    13140
tatttcttca taatccagtc ctattttatg tgtccactaa attgtttatt ttcctagaat    13200
ttttccattt attggcatat gcatgtccat agaagccttt tatagtcctt ttcatttcta    13260
gtgtcatttt tttccttttt tttaagaatc cttaagattt tagagatgaa atgtcacttt    13320
gttacgcata ctggagtgcg gtgacattat tatagctcac tgaaacccaa actcctgagt    13380
ttaagcaatc cttctacctc aaaattccaa aattcctgag tagctgagac aggcatacac    13440
catcaagact ggctaattta tttcaaattt tgtagagatg ggttcttact aagctattct    13500
caatctttgg gcttcaagtg attcttcagc ctctgtctct gaaaatgctg ggtttataga    13560
tatgagcctc tatgcctgat ttgctttgtc tctttgtaat ctcccatttt atttgtgtct    13620
tttctggttt gtttcatttt gttatgtttt cagttacctt gctaaagctt tgtcgatttt    13680
atctcttcaa acaactaact caatattttg ctgattttcc atatagtatt ttatttctat    13740
ttcatttatt tctgctctaa tctttgttaa atatcttgtt ttcctaataa ttttgagttt    13800
ccttgttctt gttttctaat tccttgcgat gttatcataa attgtttatt tgatatcttt    13860
ctactttttt gatgtgtgtg ttcgttgttg tagactttcc tctttattat tctgatttct    13920
tcctcaattc tctaatatta tgattgcatt attttccaag tttcttttgt tttttatt    13980
atagtttatg tgattcctga acttgtcaaa gagattattg tgaatttgat gtcggatatt    14040
taagcatttt caaaactttt ggtgcattat tgaaatttta ttggtttatt ttagagatgt    14100
catacttccc agttttttt taacaatact tgctctttat attgatgtct acatatttaa    14160
aaagataacc acctgattca gcttttaag gtgatatgca gtggtgttaa gtgtgtactg    14220
cttaatatca gagctgaatc actgccctga ggattcttc tgttctgagg agagcttgta    14280
gttaatagca gaacctaaat agtgcagtag agctaaatct cttccatgct gttgttttcc    14340
tgtctgggga agacttatca tgaccatgaa aacataatgc tgtgccagaa cttaaaccca    14400
aacctgtagt aatttctgag ttgaggaagg cttaagaaat aactggaact tagttactaa    14460
```

-continued

```
cctgatagtt gtttctgagt cagagaaatg ctctgcatga tcacctggga tatttgtaaa    14520
atctaaccaa agattctagc cttcccttg gattgtgcct cctgtactac tgtagtgctg     14580
gctaggtcct catcagtgaa ttccctgctg ataggaccac aaagcatctg ccaagatctg    14640
tttgccattt gctgtgatta gtgcttctgc tctttgcttc caattcaact caggtggttc    14700
agcccttctg acactcctaa tacctcctgt gggatggaac atagaaggct tctcacaatg    14760
attcacacac tgatatggag attgaatgtc cagttgcaac tattttcttc cacctgtgta    14820
attgcaggta cagggaagtt ttctgtgact gatgctattt tggtttggag aatggggtga    14880
tgtggcacaa tgatctttct tctttctggt catggatttt ttaatttcca tgaacccata    14940 agattttca cttttcttct gagctctggt gctttcagag tggtattttt atattcgaat     15000
agttgctagt tgtactttta aaagcgattg atgctggagg tcttctattc caccatctcg    15060
ctgatgtcag tcctcaaata ataatttat attttagcaa attatttgg ttttaggatt     15120 ttgtgtctac gtgacacaga catgaaaaga gatgtactca ttactgaaac tttttgcata   15180 ctgtttggt tgtgcgcctt ttctagtatg aatgattaca tatttaagcc acatgttta     15240 tacatagact gtcctttaaa gagactagat agttctgtgt gtcagcatat agggacagaa    15300
tataactaca cattaataat ttctcaagta tttattttag aagtgtaagt aacctttatt    15360 ttaattttg ttatattatg cctctgtaat gcagataaat ttttatcttc aggaaatgga    15420
aaattttgtc cagagttcag gggaagatgg tattgtggtg ttttctctgg ggtcactgtt    15480
tcaaaatgtt acagaagaaa aggctaatat cattgcttca gcccttgccc agatcccaca    15540
gaaggtcagt aaaacctcca atcctgataa gcagctattc acataatgaa acagtatggt    15600
tttatttggg tcttgaatct cattttccac ttagcataac aggtaccaaa atttgcaaaa    15660
cattatagta gtgtacatgg gcataactga tcatttgcct actgagtctt gctgttactg    15720
gaaacaactt tcttgattgt catttgttta taataaaata gatataataa ataaagctct    15780
accttatatt ttaggatttg aaatctaaaa gcgtgtgcca atgattccaa aaaaaaattc    15840
tgacatctat tatttcaaag gaccagaaaa aggaaaactg atataaaaaa aaaagaaga    15900 atcaatctca agaatatctt ctcatatttg tgtgtataaa aactgtattc agggtagttt    15960
tgcttagaaa taaagctca gattaatgta gtctttctaa ataattagaa gtttcaaaag    16020
taaaatgtca attacaatta tagtatagta acaattattt aagtaatgta attatttatg    16080
atactccact aattttaact ttattattac tgtaattcta gaatttcaca ctttagatag    16140
tgctatatat aaactatcca aaagatattt cattttatat ttagctaaaa tacttcaaac    16200
tcaataaagg caagcatact aattaggaat ttgaaatatt gtaatttcaa ttatgaaatt    16260
atctgttaag tagtttgaaa catctatgcc gttctttgtt ttcaaatgta taaaatttgt    16320
ataggtgtcc aacaaagaaa aattgtgtaa aaaaaaggta caatctcaaa gaaaatttat   16380
cattgaacag tggaacataa gtaattttct agctcattct tcttcaataa aacaattaaa    16440
tataagaaga aagaggccag gaaggaaata gagaagaaaa gacacccgat tatccaaaag   16500
acacacataa ttgaaagcaa attttatct gcagggaact gtaaatttga tggtagaatg    16560
agattggctc catgagttaa aatgacacac agatcaggta cttataaaat ttttaattct    16620
tatataaaaa tagattagcc actgctgaat tatttttta aatattcact ggtattctca    16680
ttctcaaata tttttaattg gtaataaaat aataatagca tacctaatag gcaactggta    16740
cacattattt taaagatctc ttgtaaaacg tcctactata tctttcagtc tttacgcggt    16800
```

```
agctctacac acccctgtct caaccatcac ctgaagtaca atgagtttat aatttataac    16860
tatatctaca tccttagaat gctaatatcc tgtggttcac tctgtgaaat acatgtgttt    16920
cttccgtagg tgttatggag gtacaaagga aaaaaaccat ccacattagg agccaatact    16980
cggnnnnnnn nnnnnnnnnn nnnnnnnnnn nnnnnnnnnn nnnnnnnnnn nnnnnnnnnn    17040
nnnaaaaaaa aagacccaat cccaaagaaa atttatcata gaacaatgga acataggtaa    17100
ttctctagct cattcgtctt caataaaaca aataaatata agaagacaaa ggtcaggaag    17160
gaaatagaga agaaaagata accgattatc caaaatcaca cacaaaattg aaagcaaatt    17220
ttatctgtgg ggaactgtaa atttgatggt agaaccagaa tagttccatg atttgaaatg    17280
acacagagat catgtactta taaaatattt tattcttata agaaaattga gtagccagtg    17340
ctgaattact ttttaatgat tcactgatat tctcatactc agatatttta attgatatta    17400
aaataataat agtatactta atagtcaact ggtacacatt atttgaaagg acttttgtaa    17460
aaagtcctac tatgtctttt actgtttaca cagtacctct acatacccct gtctcaacca    17520
acacctgaag tacaatgagt ttataattta taactatatc tacatcctta gagtgctaat    17580
atcctgtggt tcaatctgtg aaatacatgt gtttcttcca taggtgttat agagatacaa    17640
tggaaaaaaa accatccaca ttaggaacca atactcggct gtatgatggg ataccccaga    17700
atgatcttct tggtaggtct atgagaaagt aaaaatatga actagacgag gaaaaaatga    17760
ataaatgtta aacagcaagc aaattcagca aagatctaaa attataaaac tttatttta    17820
ttactctttt gaagcagata taattaaagg attgactaaa attgtataga ttcacactt    17880
ctattgttaa ggtgagagtg acaggaaatt cagaaggaat taatgcctat ttttctggag    17940
atagaaatga tctttagtag caatgctcca tgtgctcacc ttctaaagaa agtgctgtac    18000
gcttcagtga gttatctcgt aattcccatc tgtagttttt aaataatttt aaaagtttag    18060
aataaaatat ctcaccattt tcatccaat ttacatacta ggtcatccca aaaccaaagc    18120
ttttatcact catggtggaa tgaatgggat ctatgaagct atttaccatg gggtccctat    18180
ggtgggagtt cccatattgg gtgatcagct tgataacata gctcacatga aggccaaagg    18240
agcagctgta gaaataaact tcaaaactat gacaagcgaa gatttactga gggctttgag    18300
aacagtcatt accgattcct cgtaagtact actgcttgta cagactgatc taacattgac    18360
tatgttatac attataccag aaaatgttaa atatcatcct ggtagacatg ttgagggatt    18420
ttactccaca atattgagtc attcatcacc ttgttactgg aatagttgtg gaaattgtag    18480
ttcatagagt gtcaaacttt cttcatgaa atattaggtt taagttaaca actggcttac    18540
taagctttta ttcacatctt aatttaccc cattttgtta agaatatact ctttcagtct    18600
ctccactata tctgttaat actatgtaac caacaatatt catgtcacaa ccagaatcaa    18660
tcttttactg aacatgttct tggcttgcat aacatatact acggtttatc tacgtgtctt    18720
ttatgaaaac aaaactacaa cttctaagt tctatgtgtg tttttccctt ccagttataa    18780
agagaatgct atgagattat caagaattca ccatgatcaa cctgtaaagc ccctagatcg    18840
agcagtcttc tggatcgagt ttgtcatgcg ccacaaagga gccaagcacc tgcgatcagc    18900
tgcccatgac ctcacctggt tccagcacta ctctatagat gtgattgggt tcctgctgac    18960
ctgtgtggca actgctatat tcttgttcac aaaatgtttt tattttcct gtcaaaaatt    19020
taataaaaact agaaagatag aaaagaggga atagatcttt ccaaattcaa gaaagacctg    19080
atggggtaat cctgttaatt ccagccacat agaatttggt gaaaaccttg ctatttcat    19140
attatctatt ctgttattt atcttagcta tatagcctag aattccacga tcatgaggtt    19200
```

-continued

```
gtgagtatat ctcattcttt cgttgtattt tcctaggtgt ctttactctc ttctctcact    19260
ttgtgacaca aggacatgaa tacatctaaa ttttcctatt tctgatatga ctgttttgat    19320
gatgtcatta cttctataac cttaagtgat agggtgacat gcaatatgat tattcctggt    19380
gtgcgcccaa acacatggat ataaagaggt aaaaaactta aaattcacaa aattcagtaa    19440
accacacaaa tcaggtaagt gttctatgag attagctggc tatgagaaac ataatgatgt    19500
ttctttttca atttaaataa gcccttctac atagccagca tcagtgatct cagaaaataa    19560
attgctaata atgatgacat ggcattatgc ttagaaaagt ttgctgtatt tccatagacc    19620
tcatctagat gtcatggcct acatttctgc catcactcaa ccaatacttt tttctgtttt    19680
cttgatgata aaaagacctt tctcatgatt gccatcaaat aacaaaagaa actatttttt    19740
ttctcacata gagaacatgt cagtaagata ttcaaggtga acagatattt ttgggattag    19800
taactatttg aaatatgtgg tgataattac tgagtttata aaatttattt gatagtacac    19860
ttaaagaaga tttatatgtt tattctttaa aaatgatgaa tactcataat tcttatctct    19920
ataatcaaaa gtaaatttta ctgtagaaaa ataaagagat gcttgttctg aaagtaagat    19980
cagtgaactg cttttcagtc tcaatctttg agaattgtaa attcatcaaa taattgctta    20040
catagtaaaa atttaaggta ttagaaaacc tgcataacaa atagtattat atattaaata    20100
ttttgatatg taaagctcta cacaaagcta aatatagtgt aataatgttt acactagtaa    20160
gcaaatatgt taatcttctc attttttttac tgtcatataa tcttagtgat atgcctatta    20220
atagttttaa ataaataaat tggcttatct ggcttttga aaattttgaa attcttacag    20280
atgttgatta ggtatatcta caaattaatt tcaattttaa aatgatgata taaaaataaa    20340
tataagtatt tttcttgtgt atgtatacaa taaatataaa taaaattgtt tactgttttg    20400
aaagtttctt aagttttac actgatatgt tttttgactt ttacaatatt attataatct    20460
aggaaaagct gattatatct gttttaagcc tcatcttttc tctgtaatta aacacagtaa    20520
tttattaaca tgctgtgaca ggtgggaagc catttctgga gttgagcctg ctgacactct    20580
ggagcttttt aggttggacg ttcattgtat gtgggactct ctgcctctcg atagctgttg    20640
ctcataagac tctccttcat caatctggca ttgaattttg cgatcagttg caatcagaat    20700
ccaattggcc ttgccgtttt agtatgttct atcttaacca gcaatttcta accaggagcc    20760
tgcccaggtt tgttctgtct tccctgtaag aagctcccag cataaatatt ctaaatttta    20820
cactactaat ctattaacca acctttggac catgttcact ttaggttgag catagtgtga    20880
tgagatgcaa attaaattac aatcctatag gtgtgtgtta taaatttaa agtgtataaa    20940 ttaaataaca cattctaagt atccaacaaa ggtcaaaaaa atgatataaa gtcaccaaac    21000
```

<210> SEQ ID NO 4
<211> LENGTH: 449
<212> TYPE: PRT
<213> ORGANISM: Human

<400> SEQUENCE: 4

```
Met Pro Gln Asp Arg Thr Glu Glu Asn Glu Ile Phe Val Asp Leu Ala
 1               5                  10                  15

Leu Asn Val Leu Pro Gly Leu Ser Thr Trp Gln Ser Val Ile Lys Leu
            20                  25                  30

Asn Asp Phe Phe Val Glu Ile Arg Gly Thr Leu Lys Met Met Cys Glu
        35                  40                  45

Ser Phe Ile Tyr Asn Gln Thr Leu Met Lys Lys Leu Gln Glu Thr Asn
```

```
                    50                  55                  60
Tyr Asp Val Met Leu Ile Asp Pro Val Ile Pro Cys Gly Asp Leu Met
 65                  70                  75                  80

Ala Glu Leu Leu Ala Val Pro Phe Val Leu Thr Leu Arg Ile Ser Val
                    85                  90                  95

Gly Gly Asn Met Glu Arg Ser Cys Gly Lys Leu Pro Ala Pro Leu Ser
                100                 105                 110

Tyr Val Pro Val Pro Met Thr Gly Leu Thr Asp Arg Met Thr Phe Leu
                115                 120                 125

Glu Arg Val Lys Asn Ser Met Leu Ser Val Leu Phe His Phe Trp Ile
130                 135                 140

Gln Asp Tyr Asp Tyr His Phe Trp Glu Glu Phe Tyr Ser Lys Ala Leu
145                 150                 155                 160

Gly Arg Pro Thr Thr Leu Cys Glu Thr Val Gly Lys Ala Glu Ile Trp
                165                 170                 175

Leu Ile Arg Thr Tyr Trp Asp Phe Glu Phe Pro Gln Pro Tyr Gln Pro
                180                 185                 190

Asn Phe Glu Phe Val Gly Gly Leu His Cys Lys Pro Ala Lys Ala Leu
                195                 200                 205

Pro Lys Glu Met Glu Asn Phe Val Gln Ser Ser Gly Glu Asp Gly Ile
210                 215                 220

Val Val Phe Ser Leu Gly Ser Leu Phe Gln Asn Val Thr Glu Glu Lys
225                 230                 235                 240

Ala Asn Ile Ile Ala Ser Ala Leu Ala Gln Ile Pro Gln Lys Val Leu
                245                 250                 255

Trp Arg Tyr Lys Gly Lys Lys Pro Ser Thr Leu Gly Ala Asn Thr Arg
                260                 265                 270

Leu Tyr Asp Trp Ile Pro Gln Asn Asp Leu Leu Gly His Pro Lys Thr
                275                 280                 285

Lys Ala Phe Ile Thr His Gly Gly Met Asn Gly Ile Tyr Glu Ala Ile
290                 295                 300

Tyr His Gly Val Pro Met Val Gly Val Pro Ile Phe Gly Asp Gln Leu
305                 310                 315                 320

Asp Asn Ile Ala His Met Lys Ala Lys Gly Ala Ala Val Glu Ile Asn
                325                 330                 335

Phe Lys Thr Met Thr Ser Glu Asp Leu Leu Arg Ala Leu Arg Thr Val
                340                 345                 350

Ile Thr Asp Ser Ser Tyr Lys Glu Asn Ala Met Arg Leu Ser Arg Ile
                355                 360                 365

His His Asp Gln Pro Val Lys Pro Leu Asp Arg Ala Val Phe Trp Ile
370                 375                 380

Glu Phe Val Met Arg His Lys Gly Ala Lys His Leu Arg Ser Ala Ala
385                 390                 395                 400

His Asp Leu Thr Trp Phe Gln His Tyr Ser Ile Asp Val Ile Gly Phe
                405                 410                 415

Leu Leu Ala Cys Val Ala Thr Ala Ile Phe Leu Phe Thr Lys Cys Phe
                420                 425                 430

Leu Phe Ser Cys Gln Lys Phe Asn Lys Thr Arg Lys Ile Glu Lys Arg
                435                 440                 445

Glu

<210> SEQ ID NO 5
<211> LENGTH: 530
```

-continued

```
<212> TYPE: PRT
<213> ORGANISM: Human

<400> SEQUENCE: 5

Met Ala Pro Gly Lys Leu Ala Ser Ala Val Leu Leu Leu Leu Leu Cys
 1               5                  10                  15

Cys Ala Gly Ser Gly Phe Cys Gly Lys Val Leu Val Trp Pro Cys Glu
             20                  25                  30

Met Ser His Trp Leu Asn Leu Lys Thr Leu Leu Glu Leu Val Lys
         35                  40                  45

Arg Gly His Glu Val Thr Val Leu Thr Leu Ser Asn Asn Leu Phe Ile
 50                  55                  60

Asp Tyr Asn Arg His Pro Ala Phe Asn Phe Glu Val Ile Pro Val Pro
 65                  70                  75                  80

Thr Asp Lys Asn Met Ser Glu Asn Ile Leu Asn Glu Phe Ile Glu Leu
                 85                  90                  95

Ala Val Asn Val Met Pro Thr Met Pro Leu Trp Gln Ser Gly Lys Leu
                100                 105                 110

Leu Gln Gln Phe Phe Val Gln Ile Thr Glu Asp Leu Gly Leu Asn Cys
            115                 120                 125

Arg Asn Thr Val Tyr Asn Gln Ser Leu Met Lys Lys Leu Arg Asp Ser
130                 135                 140

Lys Tyr Asp Val Leu Val Thr Asp Pro Val Ile Pro Cys Gly Glu Leu
145                 150                 155                 160

Val Ala Glu Met Leu Gly Val Pro Phe Val Asn Met Leu Lys Phe Ser
                165                 170                 175

Met Gly His Thr Ile Glu Lys Tyr Cys Gly Gln Leu Pro Ala Pro Pro
            180                 185                 190

Ser Tyr Val Pro Val Pro Leu Gly Gly Leu Thr Thr Arg Met Thr Phe
        195                 200                 205

Met Glu Arg Val Lys Asn Met Val Phe Ser Val Leu Phe Asp Phe Trp
    210                 215                 220

Ile Gln Gln Tyr Asp Tyr Lys Phe Trp Asp Gln Phe Tyr Ser Glu Ala
225                 230                 235                 240

Leu Gly Arg Pro Thr Thr Leu Cys Glu Ile Met Gly Lys Ala Glu Ile
                245                 250                 255

Trp Leu Ile Arg Thr Tyr Trp Asp Phe Glu Phe Pro Arg Pro Tyr Leu
            260                 265                 270

Pro Asn Phe Glu Phe Val Gly Gly Leu His Cys Lys Pro Ala Lys Pro
        275                 280                 285

Leu Pro Lys Glu Met Glu Glu Phe Val Gln Ser Ser Gly Glu Asp Gly
    290                 295                 300

Val Val Val Phe Ser Leu Gly Ser Met Val Lys Asn Leu Thr Glu Glu
305                 310                 315                 320

Lys Ala Asn Leu Ile Ala Ser Ala Leu Ala Gln Ile Pro Gln Lys Val
                325                 330                 335

Leu Trp Arg Tyr Lys Gly Lys Lys Pro Ala Thr Leu Gly Pro Asn Thr
            340                 345                 350

Arg Leu Phe Asp Trp Ile Pro Gln Asn Asp Leu Leu Gly His Pro Lys
        355                 360                 365

Thr Lys Ala Phe Ile Thr His Gly Gly Ser Asn Gly Ile Tyr Glu Ala
    370                 375                 380

Ile Tyr His Gly Val Pro Met Val Gly Met Pro Ile Phe Ser Asp Gln
385                 390                 395                 400
```

-continued

```
Pro Asp Asn Leu Ala Gly Met Lys Ala Lys Gly Ala Ala Val Glu Val
            405                 410                 415

Asn Met Asn Thr Met Thr Ser Ala Asp Leu Leu Gly Ala Leu Arg Thr
            420                 425                 430

Val Ile Asn Asp Pro Thr Tyr Lys Glu Asn Ala Met Lys Leu Ser Arg
            435                 440                 445

Ile His His Asp Gln Pro Val Lys Pro Leu Asp Arg Ala Ala Phe Trp
        450                 455                 460

Val Glu Phe Val Met His His Lys Gly Ala Lys His Leu Arg Val Ala
465                 470                 475                 480

Ala His Asp Leu Ser Trp Phe Gln Tyr His Ser Leu Asp Val Ile Gly
                485                 490                 495

Phe Leu Leu Ala Cys Val Ala Ser Ala Ile Leu Leu Val Thr Lys Cys
                500                 505                 510

Cys Leu Phe Ser Phe Gln Asn Phe Ile Lys Ile Gly Lys Arg Ile Lys
            515                 520                 525

Lys Glu
    530
```